US010874512B2

(12) United States Patent
von Oepen et al.

(10) Patent No.: US 10,874,512 B2
(45) Date of Patent: *Dec. 29, 2020

(54) SYSTEM AND METHODS FOR DELIVERING AND DEPLOYING AN ARTIFICIAL HEART VALVE WITHIN THE MITRAL ANNULUS

(71) Applicants: Randolf von Oepen, Aptos, CA (US); Sean A. McNiven, Menlo Park, CA (US); Francisco Valencia, East Palo Alto, CA (US)

(72) Inventors: Randolf von Oepen, Aptos, CA (US); Sean A. McNiven, Menlo Park, CA (US); Francisco Valencia, East Palo Alto, CA (US)

(73) Assignee: Cephea Valve Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/724,499

(22) Filed: Oct. 4, 2017

(65) Prior Publication Data
US 2018/0092744 A1  Apr. 5, 2018

Related U.S. Application Data

(60) Provisional application No. 62/462,776, filed on Feb. 23, 2017, provisional application No. 62/436,922, (Continued)

(51) Int. Cl.
*A61F 2/24* (2006.01)
*A61F 2/95* (2013.01)

(52) U.S. Cl.
CPC .......... *A61F 2/2436* (2013.01); *A61F 2/2439* (2013.01); *A61F 2/2409* (2013.01);
(Continued)

(58) Field of Classification Search
CPC .... A61F 2/2409; A61F 2/2436; A61F 2/2439; A61F 2/2427; A61F 2002/9517; A61F 2002/9522; A61F 2210/0014
See application file for complete search history.

(56) References Cited

U.S. PATENT DOCUMENTS 4,406,656 A  9/1983  Hattler et al.
4,728,319 A  3/1988  Masch
(Continued)

FOREIGN PATENT DOCUMENTS

CN  1469724  1/2004
CN  101506538 A  8/2009
(Continued)

OTHER PUBLICATIONS

Hironobu Takizawa et al. "Development of a Microfine Active Bending Catheter Equipped with MIF Tactile Sensors", Micro Electro Mechanical Systems, IEEE, Jan. 17, 1999, pp. 412-417.
(Continued)

*Primary Examiner* — Jocelin C Tanner
(74) *Attorney, Agent, or Firm* — Workman Nydegger

(57) ABSTRACT

The present disclosure describes devices, systems, and methods for loading, delivering, positioning, and deploying an artificial heart valve device at the mitral annulus. A delivery system includes a delivery member coupled to a handle assembly and extending distally from the handle assembly. The valve device is attached at the distal end of the delivery member, and is constrained within a valve cover of an outer sheath. A delivery catheter is configured to advance the valve relative to the outer sheath, and a suture catheter includes sutures/tethers which maintain proximal tension on the valve prior to deployment.

20 Claims, 21 Drawing Sheets

Related U.S. Application Data filed on Dec. 20, 2016, provisional application No. 62/430,149, filed on Dec. 5, 2016, provisional application No. 62/404,511, filed on Oct. 5, 2016.

(52) U.S. Cl.
CPC .......... *A61F 2/9517* (2020.05); *A61F 2/9522* (2020.05); *A61F 2210/0014* (2013.01)

(56) References Cited

U.S. PATENT DOCUMENTS

| | | |
|---|---|---|
| 5,053,043 A | 10/1991 | Gottesman et al. |
| 5,059,213 A | 10/1991 | Chesterfield et al. |
| 5,078,722 A | 1/1992 | Stevens |
| 5,078,723 A | 1/1992 | Dance et al. |
| 5,236,450 A | 8/1993 | Scott |
| 5,325,845 A | 7/1994 | Adair |
| 5,345,945 A | 9/1994 | Hodgson et al. |
| 5,387,219 A | 2/1995 | Rappe |
| 5,415,664 A | 5/1995 | Pinchuk |
| 5,472,423 A | 12/1995 | Gronauer |
| 5,571,085 A | 11/1996 | Accisano, III |
| 5,662,606 A | 9/1997 | Cimino et al. |
| 5,669,919 A | 9/1997 | Sanders et al. |
| 5,769,812 A | 6/1998 | Stevens et al. |
| 5,807,405 A | 9/1998 | Vanney et al. |
| 5,820,591 A | 10/1998 | Thompson et al. |
| 5,843,103 A | 12/1998 | Wulfman |
| 5,855,601 A | 1/1999 | Bessler et al. |
| 5,873,882 A | 2/1999 | Straub et al. |
| 5,902,334 A | 5/1999 | Dwyer et al. |
| 5,906,642 A | 5/1999 | Caudillo et al. |
| 5,957,973 A | 9/1999 | Quiachon et al. |
| 6,090,118 A | 7/2000 | McGuckin, Jr. |
| 6,180,059 B1 | 1/2001 | Divino, Jr. et al. |
| 6,228,110 B1 | 5/2001 | Munsinger |
| 6,458,137 B1 | 10/2002 | Klint |
| 6,517,550 B1 | 2/2003 | Konya et al. |
| 6,695,836 B1 | 2/2004 | DeMello et al. |
| 6,926,725 B2 | 8/2005 | Cooke et al. |
| 7,172,617 B2 | 2/2007 | Colgan et al. |
| 7,344,553 B2 | 3/2008 | Opolski et al. |
| 7,666,204 B2 | 2/2010 | Thornton et al. |
| 7,736,388 B2 | 6/2010 | Goldfarb et al. |
| 7,837,727 B2 | 11/2010 | Goetz et al. |
| 7,988,724 B2 | 8/2011 | Salahieh et al. |
| 7,993,303 B2 | 8/2011 | Von Oepen et al. |
| 8,157,852 B2 | 4/2012 | Bloom et al. |
| 8,523,881 B2 | 9/2013 | Cabiri et al. |
| 8,647,323 B2 | 2/2014 | Guo et al. |
| 8,911,455 B2 | 12/2014 | Quadri et al. |
| 8,926,588 B2 | 1/2015 | Berthiaume et al. |
| 8,926,692 B2 | 1/2015 | Dwork |
| 9,339,378 B2 | 5/2016 | Quadri et al. |
| 9,370,423 B2 | 6/2016 | Ryan |
| 9,393,112 B2 | 7/2016 | Tuval et al. |
| 9,399,112 B2 | 7/2016 | Shevgoor et al. |
| 9,668,859 B2 | 6/2017 | Kheradvar et al. |
| 9,687,373 B2 | 6/2017 | Vad |
| 9,693,862 B2 | 7/2017 | Campbell et al. |
| 9,801,745 B2 | 10/2017 | Wubbeling et al. |
| 10,111,671 B2 | 10/2018 | Bodewadt |
| 10,117,760 B2 | 11/2018 | Mangiardi |
| 10,376,673 B2 | 8/2019 | Van Hoven et al. |
| 10,398,553 B2 | 9/2019 | Kizuka |
| 10,470,902 B2 | 11/2019 | Sheldon et al. |
| 2001/0002445 A1 | 5/2001 | Vesely |
| 2001/0047150 A1 | 11/2001 | Chobotov |
| 2002/0013547 A1 | 1/2002 | Paksar |
| 2004/0049207 A1 | 3/2004 | Goldfarb et al. |
| 2004/0064179 A1 | 4/2004 | Linder et al. |
| 2004/0116848 A1 | 6/2004 | Gardeski et al. |
| 2004/0127849 A1 | 7/2004 | Kantor |
| 2004/0133232 A1 | 7/2004 | Rosenbluth et al. |
| 2004/0147826 A1 | 7/2004 | Peterson |
| 2005/0038383 A1 | 2/2005 | Kelley et al. |
| 2005/0085903 A1 | 4/2005 | Lau |
| 2005/0137695 A1 | 6/2005 | Salahieh et al. |
| 2005/0143809 A1 | 6/2005 | Salahieh et al. |
| 2005/0256452 A1 | 11/2005 | DeMarchi et al. |
| 2005/0259452 A1 | 11/2005 | DeMarchi et al. |
| 2005/0283231 A1 | 11/2005 | Haug et al. |
| 2005/0277874 A1 | 12/2005 | Selkee |
| 2005/0277876 A1 | 12/2005 | Hayden |
| 2006/0135961 A1 | 6/2006 | Rosenman et al. |
| 2007/0060997 A1 | 3/2007 | de Boer |
| 2007/0156225 A1 | 7/2007 | George et al. |
| 2007/0173757 A1 | 7/2007 | Levine et al. |
| 2007/0197858 A1 | 8/2007 | Goldfarb et al. |
| 2007/0203561 A1 | 8/2007 | Forster et al. |
| 2007/0260225 A1 | 11/2007 | Sakakine et al. |
| 2007/0270779 A1 | 11/2007 | Jacobs et al. |
| 2007/0299424 A1 | 12/2007 | Cumming et al. |
| 2008/0103585 A1 | 5/2008 | Monstadt et al. |
| 2008/0188850 A1 | 8/2008 | Mody et al. |
| 2008/0195126 A1 | 8/2008 | Solem |
| 2009/0036768 A1 | 2/2009 | Seehusen et al. |
| 2009/0069885 A1* | 3/2009 | Rahdert ............ A61B 17/0401 623/2.1 |
| 2009/0099554 A1 | 4/2009 | Forester et al. |
| 2009/0163934 A1 | 6/2009 | Raschdorf, Jr. et al. |
| 2009/0204005 A1 | 8/2009 | Keast et al. |
| 2009/0240326 A1 | 9/2009 | Wilson et al. |
| 2009/0276039 A1 | 11/2009 | Meretei |
| 2009/0281619 A1 | 11/2009 | Le et al. |
| 2010/0004739 A1 | 1/2010 | Vesely |
| 2010/0044410 A1 | 2/2010 | Argentine et al. |
| 2010/0059173 A1 | 3/2010 | Kampa et al. |
| 2010/0217261 A1 | 8/2010 | Watson |
| 2010/0249894 A1 | 9/2010 | Oba et al. |
| 2010/0331776 A1 | 12/2010 | Salahieh et al. |
| 2011/0112630 A1 | 5/2011 | Groothuis et al. |
| 2011/0166566 A1 | 7/2011 | Gabriel |
| 2011/0166649 A1 | 7/2011 | Gross et al. |
| 2011/0202128 A1 | 8/2011 | Duffy |
| 2011/0257718 A1 | 10/2011 | Argentine |
| 2011/0307049 A1 | 12/2011 | Kao |
| 2012/0022640 A1 | 1/2012 | Gross et al. |
| 2012/0065464 A1 | 3/2012 | Ellis et al. |
| 2012/0109078 A1 | 5/2012 | Schaeffer |
| 2012/0172915 A1 | 7/2012 | Fifer et al. |
| 2012/0316639 A1 | 12/2012 | Kleinschrodt |
| 2012/0330348 A1 | 12/2012 | Strauss et al. |
| 2012/0330408 A1 | 12/2012 | Hillukka et al. |
| 2013/0041314 A1 | 2/2013 | Dillon |
| 2013/0066342 A1 | 3/2013 | Dell et al. |
| 2013/0103001 A1 | 4/2013 | BenMaamer et al. |
| 2013/0131775 A1 | 5/2013 | Hadley et al. |
| 2014/0107693 A1 | 4/2014 | Plassman |
| 2014/0114390 A1 | 4/2014 | Tobis et al. |
| 2014/0142688 A1 | 5/2014 | Duffy et al. |
| 2014/0148889 A1 | 5/2014 | Deshmukh et al. |
| 2014/0180124 A1 | 6/2014 | Whiseant et al. |
| 2014/0200649 A1 | 7/2014 | Essinger et al. |
| 2014/0228871 A1 | 8/2014 | Cohen et al. |
| 2014/0276966 A1 | 9/2014 | Ranucci et al. |
| 2014/0324164 A1 | 10/2014 | Gross et al. |
| 2014/0336744 A1 | 11/2014 | Tani et al. |
| 2014/0379074 A1 | 12/2014 | Spence |
| 2015/0005704 A1 | 1/2015 | Heisel et al. |
| 2015/0005801 A1 | 1/2015 | Marquis et al. |
| 2015/0088189 A1 | 3/2015 | Paul, Jr. |
| 2015/0112430 A1 | 4/2015 | Creaven et al. |
| 2015/0272759 A1 | 10/2015 | Argentine |
| 2015/0306806 A1 | 10/2015 | Dando et al. |
| 2016/0045311 A1 | 2/2016 | McCann et al. |
| 2016/0074163 A1 | 3/2016 | Yang et al. |
| 2016/0113765 A1* | 4/2016 | Ganesan ............... A61F 2/2418 623/2.11 |
| 2016/0143661 A1 | 5/2016 | Wood et al. |
| 2017/0035566 A1 | 2/2017 | Krone et al. |
| 2017/0042678 A1* | 2/2017 | Ganesan ............... A61B 90/50 |
| 2017/0080186 A1 | 3/2017 | Salahieh et al. |
| 2017/0232238 A1 | 8/2017 | Biller et al. |

(56) References Cited

U.S. PATENT DOCUMENTS

| | | |
|---|---|---|
| 2018/0028177 A1 | 2/2018 | von Oepen et al. |
| 2018/0028215 A1 | 2/2018 | Cohen |
| 2018/0028305 A1 | 2/2018 | von Oepen et al. |
| 2018/0028779 A1 | 2/2018 | von Oepen et al. |
| 2018/0028787 A1 | 2/2018 | McNiven et al. |
| 2018/0055636 A1 | 3/2018 | Valencia et al. |
| 2018/0055637 A1 | 3/2018 | von Oepen et al. |
| 2018/0056033 A1 | 3/2018 | von Oepen et al. |
| 2018/0056043 A1 | 3/2018 | von Oepen et al. |
| 2018/0071098 A1 | 3/2018 | Alon |
| 2018/0126119 A1 | 5/2018 | McNiven et al. |
| 2018/0133454 A1 | 5/2018 | von Oepen et al. |
| 2018/0360457 A1 | 12/2018 | Ellis et al. |
| 2019/0030285 A1 | 1/2019 | Prabhu et al. |
| 2019/0274831 A1 | 9/2019 | Prabhu |
| 2020/0155804 A1 | 5/2020 | von Oepen et al. |

FOREIGN PATENT DOCUMENTS

| | | |
|---|---|---|
| CN | 102258402 A | 11/2011 |
| CN | 102481433 A | 5/2012 |
| CN | 102770080 | 11/2012 |
| CN | 103517689 A | 1/2014 |
| CN | 103702635 A | 4/2014 |
| CN | 103841899 | 6/2014 |
| CN | 104812439 A | 7/2015 |
| EP | 1980288 | 4/2008 |
| EP | 2537487 | 12/2012 |
| EP | 2702965 | 3/2014 |
| EP | 3009103 | 4/2016 |
| JP | 2003062072 | 3/2003 |
| JP | 2006528911 | 12/2006 |
| JP | 2013516244 | 5/2013 |
| WO | WO 0151114 | 7/2001 |
| WO | WO 2007044285 | 4/2007 |
| WO | WO 2007136829 | 11/2007 |
| WO | WO 2008103722 | 8/2008 |
| WO | WO 2010024801 | 3/2010 |
| WO | WO 2010121076 | 10/2010 |
| WO | WO 2012020521 | 2/2012 |
| WO | 2012/057983 A1 | 5/2012 |
| WO | WO 2012151396 | 11/2012 |
| WO | WO 2014064694 | 5/2014 |
| WO | WO 2014121280 | 8/2014 |
| WO | WO 2014128705 | 8/2014 |
| WO | WO 2015191938 | 12/2015 |
| WO | WO 2016022797 | 2/2016 |
| WO | WO 2016112085 | 7/2016 |
| WO | WO 2016144708 | 9/2016 |
| WO | WO 2016150806 | 9/2016 |
| WO | WO 2016183526 | 11/2016 |
| WO | WO 2018023038 | 2/2018 |
| WO | WO 2018023043 | 2/2018 |
| WO | WO 2018023044 | 2/2018 |
| WO | WO 2018023045 | 2/2018 |
| WO | WO 2018023052 | 2/2018 |
| WO | WO 2018044446 | 3/2018 |
| WO | WO 2018044447 | 3/2018 |
| WO | WO 2018044448 | 3/2018 |
| WO | WO 2018044449 | 3/2018 |
| WO | WO 2018067788 | 4/2018 |
| WO | WO 2018093426 | 5/2018 |

OTHER PUBLICATIONS

U.S. Appl. No. 15/662,001, dated Jun. 20, 2019, Office Action.
U.S. Appl. No. 15/662,001, dated Oct. 4, 2019, Office Action.
U.S. Appl. No. 15/662,001, dated Dec. 18, 2019, Notice of Allowance.
U.S. Appl. No. 15/662,013, dated Dec. 5, 2019, Advisory Action.
U.S. Appl. No. 15/662,066, dated Jul. 11, 2019, Office Action.
U.S. Appl. No. 15/662,066, dated Dec. 16, 2019, Office Action.
U.S. Appl. No. 15/662,142, dated Dec. 20, 2019, Advisory Action.
U.S. Appl. No. 15/662,076, dated Oct. 8, 2019, Notice of Allowance.
U.S. Appl. No. 15/662,076, dated Jan. 31, 2020, Notice of Allowance.
U.S. Appl. No. 15/662,089, dated Oct. 7, 2019, Office Action.
U.S. Appl. No. 15/662,089, dated Jan. 10, 2020, Office Action.
U.S. Appl. No. 15/662,093, dated Mar. 7, 2019, Office Action.
U.S. Appl. No. 15/662,093, dated Aug. 29, 2019, Office Action.
U.S. Appl. No. 15/662,093, dated Dec. 3, 2019, Office Action.
U.S. Appl. No. 15/662,008, dated Sep. 13, 2019, Office Action.
U.S. Appl. No. 15/662,008, dated Jan. 31, 2020, Notice of Allowance.
U.S. Appl. No. 15/662,014, dated May 31, 2019, Office Action.
U.S. Appl. No. 15/662,014, dated Oct. 2, 2019, Notice of Allowance.
U.S. Appl. No. 15/662,014, dated Jan. 23, 2020, Notice of Allowance.
U.S. Appl. No. 15/662,098, dated Jul. 5, 2019 Office Action.
U.S. Appl. No. 15/662,098, dated Jan. 27, 2020, Office Action.
U.S. Appl. No. 15/662,001, dated Mar. 24, 2020, Notice of Allowance.
U.S. Appl. No. 15/662,098, dated Mar. 23, 2020, Advisory Action.
U.S. Appl. No. 15/662,013, dated May 7, 2020, NOA.
U.S. Appl. No. 15/662,093, dated May 6, 2020, OA.
U.S. Appl. No. 15/662,066, dated May 21, 2020, OA.
U.S. Appl. No. 15/662,142, dated Apr. 17, 2020, Office Action.
U.S. Appl. No. 15/662,098, dated Apr. 30, 2020, Office Action.
U.S. Appl. No. 15/662,013, dated Jun. 13, 2019, Office Action.
U.S. Appl. No. 15/662,013, dated Oct. 10, 2019, Office Action.
U.S. Appl. No. 15/662,066, dated Feb. 27, 2020, Advisory Action.
U.S. Appl. No. 15/662,089, dated Jun. 11, 2020, Office Action.

* cited by examiner

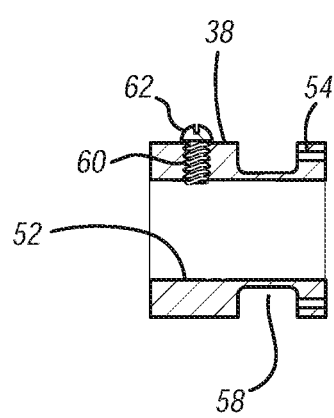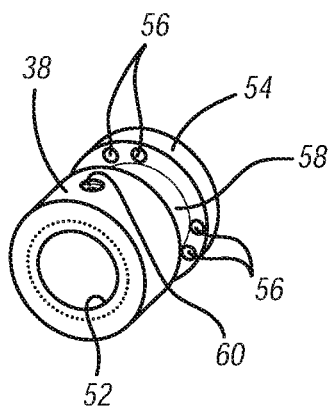
FIG. 10A  FIG. 10B

SYSTEM AND METHODS FOR DELIVERING AND DEPLOYING AN ARTIFICIAL HEART VALVE WITHIN THE MITRAL ANNULUS

CROSS-REFERENCE TO RELATED APPLICATIONS

This application claims the benefit of and priority to: U.S. Provisional Patent Application Ser. No. 62/404,511, filed Oct. 5, 2016 and titled "Systems and Methods for Loading and Deploying an Intravascular Device"; U.S. Provisional Patent Application Ser. No. 62/430,149, filed on Dec. 5, 2016 and titled "Systems and Methods for Loading and Deploying an Intravascular Device"; U.S. Provisional Patent Application Ser. No. 62/436,922, filed Dec. 20, 2016 and titled "Systems and Methods for Loading and Deploying an Intravascular Device"; and U.S. Provisional Patent Application Ser. No. 62/462,776, filed on Feb. 23, 2017 and titled "Systems and Methods for Loading and Deploying an Intravascular Device," the disclosures of which are incorporated herein by references in their entireties.

BACKGROUND

1. Field of the Invention

The present disclosure generally relates to devices, systems, and methods for loading a replacement heart valve into a delivery system, delivering the replacement heart valve to the targeted anatomy within the heart, and deploying the replacement heart valve at the targeted location.

2. The Relevant Technology

Intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. The intravascular procedure also enables faster recovery times with lower associated costs and risks of complication. An example of an intravascular procedure that significantly reduces procedure and recovery time and cost over conventional open surgery is a heart valve replacement or repair procedure. An artificial valve is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more deflecting mechanisms, which can be achieved by tension cable, or other mechanisms positioned inside the catheter. Precise control of the distal end of the catheter allows for more reliable and faster positioning of a medical device and/or implant and other improvements in the procedures.

An intravascularly delivered device needs to be placed precisely to ensure a correct positioning of the medical device, which is essential for its functionality, as the device may be difficult to reposition after the device is fully deployed from the delivery system. Additionally, the ability to recapture a partially deployed device is desirable in the event that the distal end of the catheter moves relative to the target location and compromises the precise positioning of the device.

Implanting a replacement heart valve through an intravascular approach involves several challenges. Replacement heart valve devices typically must be much larger and more complex than other interventional devices such as valve clips or annuloplasty devices. This makes loading, delivery, and deployment of the heart valve difficult. Further, replacement heart valves cannot typically be pre-loaded into the associated delivery system during manufacture, and must be loaded just prior to the implantation procedure. Artificial valves are typically stored in a glutaraldehyde solution in a storage container during storage and shipment, until the valve is attached to the delivery system just prior to the procedure. What is needed is a delivery system that can load a replacement heart valve, deliver the heart valve intravascularly to the targeted cardiac valve, properly position and orient the valve, and deploy the valve at the targeted cardiac anatomy.

BRIEF SUMMARY

The present disclosure describes devices, systems, and methods for loading a replacement heart valve device into a delivery system, intravascularly delivering the replacement heart valve device to a targeted cardiac valve using the delivery system, and deploying the replacement heart valve device at the cardiac valve.

In one embodiment, a delivery system for intravascularly delivering a replacement heart valve to a targeted cardiac valve includes a handle assembly, an elongated delivery member, and an expandable replacement heart valve device. The delivery member has a proximal end and a distal end. The proximal end of the delivery member is coupled to the handle assembly and the delivery member extends distally from the handle assembly to its distal end. The delivery member is configured to detachably couple to the expandable replacement heart valve at the distal end. The delivery member also includes an outer sheath having a valve cover configured to constrain the valve in a compressed configuration, a steering component configured to curve/steer the delivery member to enable intravascular delivery of the delivery member to the targeted cardiac valve, a delivery catheter configured to longitudinally translate the valve relative to the outer sheath during deployment, and a suture catheter having one or more tethers configured to detachably couple to a proximal section of the valve, the suture catheter being longitudinally translatable relative to the delivery catheter to enable adjustment of tension in the one or more tethers.

In some embodiments, the delivery catheter includes a compression coil at least at a distal section. The delivery catheter may include a distal cap (also referred to as a can) configured in size and shape to constrain a proximal section of the valve when the valve is held in the compressed configuration, the distal cap thereby relieving expansion pressure against an inner surface of the valve cover.

In some embodiments, the suture catheter includes a connecting ring detachably connected to a distal end of the suture catheter. A plurality of tethers may be coupled to the connecting ring and extend distally from the connecting ring.

Other embodiments may include a pre-assembled heart valve assembly, in which a plurality of tethers are attached between the heart valve and a connecting ring and placed under tension to maintain the connection between the heart valve, the tethers and the connecting ring, and the connecting ring provides a convenient and easy way to connect the heart valve assembly to the distal end of the suture catheter. In some embodiments, the heart valve assembly can be packaged as a pre-assembled unit in a sterile and/or sterilizing solution.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

In order to describe various features and concepts of the present disclosure, a more particular description of certain subject matter will be rendered by reference to specific embodiments which are illustrated in the appended drawings. Understanding that these figures depict just some example embodiments and are not to be considered to be limiting in scope, various embodiments will be described and explained with additional specificity and detail through the use of the accompanying drawings in which:

FIGS. 10A and 10B illustrate cross-sectional and perspective views, respectively, of an embodiment of a suture ring of the heart valve assembly;

DETAILED DESCRIPTION

Introduction

The present disclosure is directed to devices, systems, and methods for loading, delivering, positioning, and deploying a replacement heart valve device. Throughout this disclosure, many examples are described in the context of a replacement artificial mitral valve. One of skill in the art will understand, however, that the described components, features, and principles may also be utilized in other applications. For example, at least some of the embodiments described herein may be utilized for loading, delivering, positioning, and deploying an artificial valve for replacing a pulmonary, aortic, or tricuspid valve.

Moreover, it will be understood that at least some of the delivery system embodiments described herein may be utilized in conjunction with other interventional devices, including valve repair devices, annuloplasty devices, clip devices, and other interventional devices not necessarily configured as a replacement valve. Thus, although the following description will typically refer specifically to a replacement mitral valve device, it will be understood that the same description may be applied to embodiments which utilize other suitable interventional devices in other interventional procedures.

Notwithstanding such alternative applications, preferred embodiments described herein are configured to address challenges particularly associated with loading, delivering, positioning, and deploying an artificial replacement heart valve device. For example, where relatively simple catheters may be suitable for delivery of a clip or other such repair device, the larger size and/or more complex geometry of a replacement valve requires more robust delivery system features to properly load, deliver, and deploy the device. The embodiments described below are therefore particularly useful in for meeting the additional procedural challenges associated with heart valve replacement through an intravascular approach.

Delivery System Overview

Figure 1A:
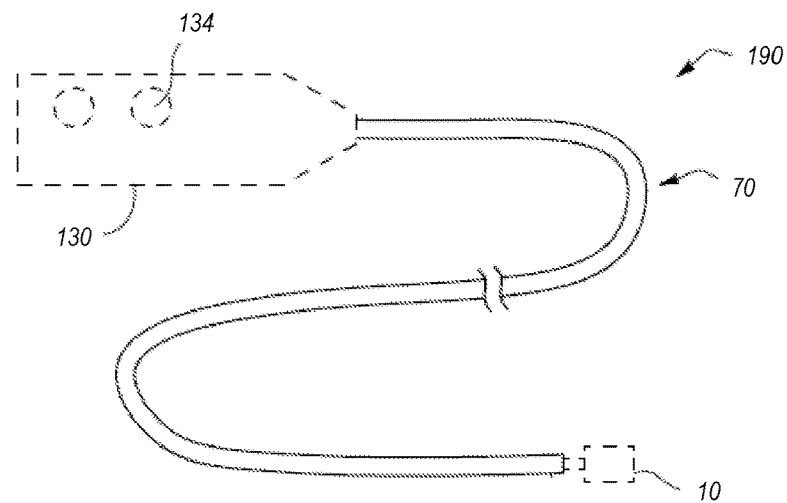
FIG. 1A schematically illustrates a delivery system that may be used to deliver a replacement heart valve to the mitral annulus.

FIG. 1A illustrates an embodiment of a delivery system 190. As shown, the delivery system 190 includes a handle assembly 130 and an elongated delivery member 70 (also referred to herein as simply the elongated member or the delivery member). The delivery member 70 is coupled to the handle assembly 130 and extends distally from the handle assembly 130. The delivery member 70 may include a plurality of catheter and/or hypotube members which provide various functionality during operation of the delivery system 190 to enable effective delivery and deployment of a replacement heart valve 10 (shown here in simplified form).

The handle assembly 130 may include one or more controls 134 operatively coupled to the delivery member to enable steering and/or manipulation of the delivery member 70 and/or other components of the delivery system 190.

Figure 1B:
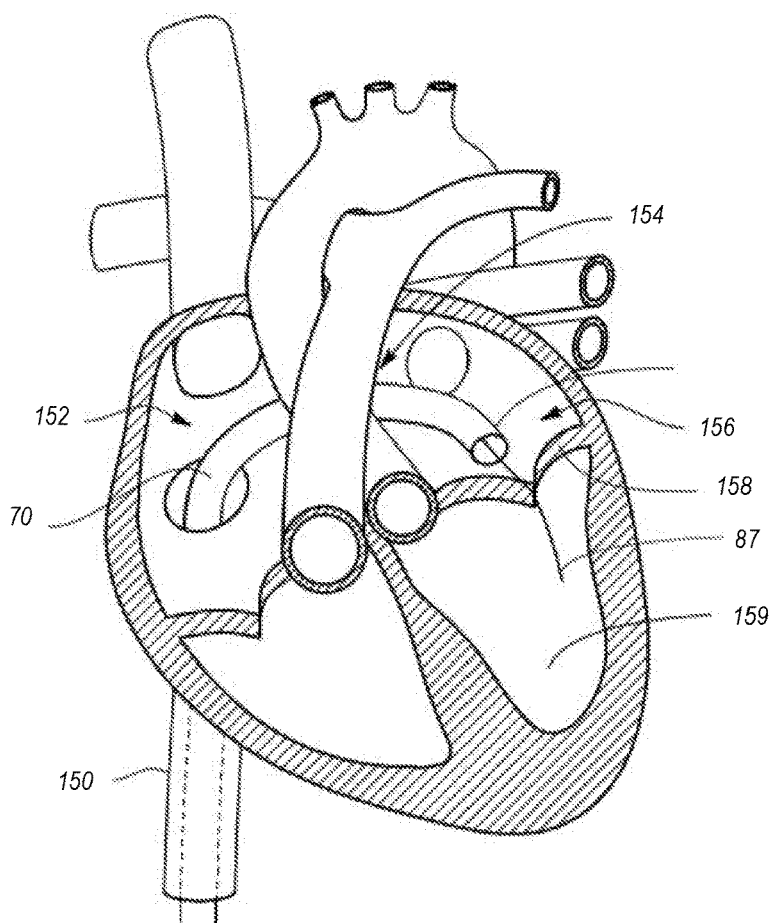
FIG. 1B provides a schematic representation of a patient's heart and illustrates an exemplary approach for delivering the replacement heart valve to the mitral annulus using the delivery system of FIG. 1A.

FIG. 1B illustrates a schematic representation of a patient's heart and a delivery procedure that may be conducted using the illustrated delivery system 190. The delivery member 70 may be inserted into the patient's vasculature (e.g., through a transfemoral approach) and directed to the inferior vena cava 150. The delivery member 70 is passed through the inferior vena cava 150 toward the heart. Upon entering the heart from the inferior vena cava 150, the delivery member 70 enters the right atrium 152. For replacement mitral valve procedures, the delivery member 70 must further pass into the left atrium 156 by passing through a puncture in the intra-atrial septum 154.

In other implementations, such as for procedures associated with a tricuspid valve, the delivery member 70 may be passed through the inferior vena cava 150 and into the right atrium 152, where it may then be positioned and used to perform the procedure related to the tricuspid valve. As described above, although many of the examples described herein are directed to mitral valve replacement, one or more embodiments may be utilized in other cardiac procedures, including those involving the tricuspid valve.

Although a transfemoral approach for accessing a targeted cardiac valve is one preferred method, it will be understood that the embodiments described herein may also be utilized where alternative approaches are used. For example, embodiments described herein may be utilized in a transjugular approach, transapical approach, or other suitable approach to the targeted anatomy. For procedures related to the mitral valve or tricuspid valve, delivery of the replacement valve or other interventional device is preferably carried out from an atrial aspect (i.e., with the distal end of the delivery member 70 positioned within the atrium superior to the targeted valve). The illustrated embodiments are shown from such an atrial aspect. However, it will be understood that the interventional device embodiments described herein may also be delivered from a ventricular aspect. In some embodiments, a guidewire 87 is utilized in conjunction with the delivery member 70.

Additional Details of Elongated Member Components

Figure 2:
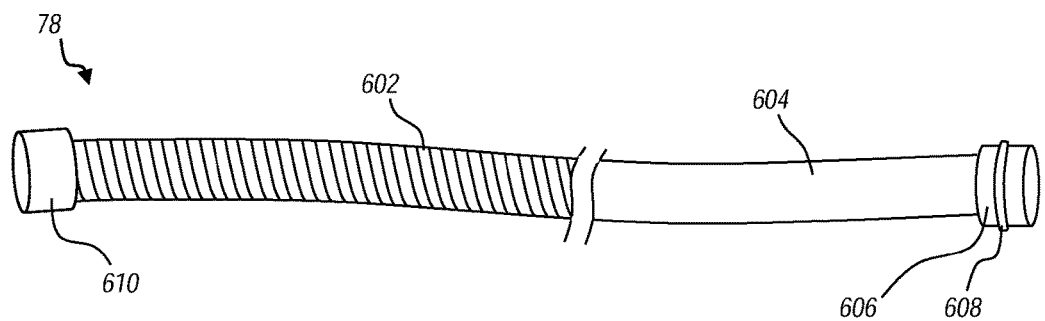
FIG. 2 illustrates a delivery catheter with distal cap configured for maintaining the replacement heart valve in a compressed configuration pre-deployment.

FIG. 2 illustrates one embodiment of a delivery catheter 78 which is housed and translatable within the outer sheath of the delivery member 70. The delivery catheter 78 includes a proximal section 604 and a distal section 602. At the proximal end, the delivery catheter 78 includes a seal 606 and an o-ring 608 for forming a fluid tight seal at the handle assembly 130. In the illustrated embodiment, the distal section 602 is formed as a compression coil. The compression coil provides the delivery catheter 78 with ability to effectively push the valve device through the steering catheter 80 as part of deploying the valve device. The compression coil also provides good flexibility for navigating a patient's tortuous vasculature.

The delivery catheter 78 also includes a can structure 610 (i.e., "distal cap") disposed at the distal end. The can 610 is configured to constrain and hold a proximal (i.e., atrial) section of the valve device. Without such constraint, the arms of the valve device would be biased radially outward against the inner surface of the outer sheath, making it more difficult to unsheathe or re-sheathe the valve. The can 610 also has a length sufficient to aid in maintaining coaxial alignment of the distal end of the delivery catheter 78 within the delivery member 70 to avoid or minimize unwanted tilting. For example, the can 610 preferably has a length to diameter ration of greater than or equal to 1, though in alternative embodiments the ratio may be smaller, such as about 0.25 to 1, depending on the stiffness of the distal section 602. The can 610 also provides an effective structural surface for acting as a counterforce to maintain the valve in position when the outer sheath 82 is retracted. In some embodiments, the proximal section of the can 610 includes a taper and/or smooth surface for easier sliding of the can 610 back into the sheath 82.

Figure 3:
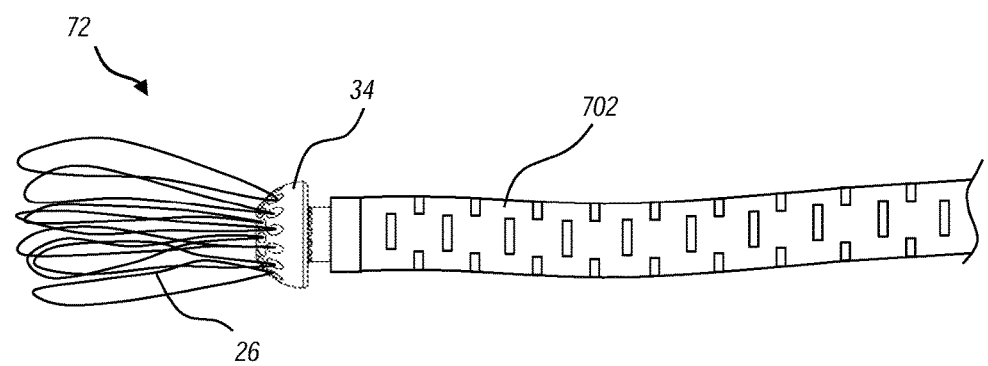
FIG. 3 illustrates an exemplary suture catheter that may be disposed within the delivery catheter of FIG. 2 and which is configured for controlling axial tension on the replacement heart valve.

FIG. 3 illustrates one embodiment of a suture catheter 72 configured to maintain axial tension of the valve device prior to deployment. As explained in more detail below, the suture catheter 72 is housed within and translatable within the delivery catheter 78. The suture catheter 72 includes a tube section formed as a cut hypotube (e.g., laser cut) to provide desired flexibility characteristics. A connecting ring 34 is attached at the distal end. The connecting ring 34 includes a tapered, angular surface for more effective advancing through the delivery member 70. A series of suture loops 26 are connected to the connecting ring 34. As explained in greater detail below, the suture loops 26 tether to corresponding attachment points or members of the valve device.

Loading of the Valve Device

Figure 4:
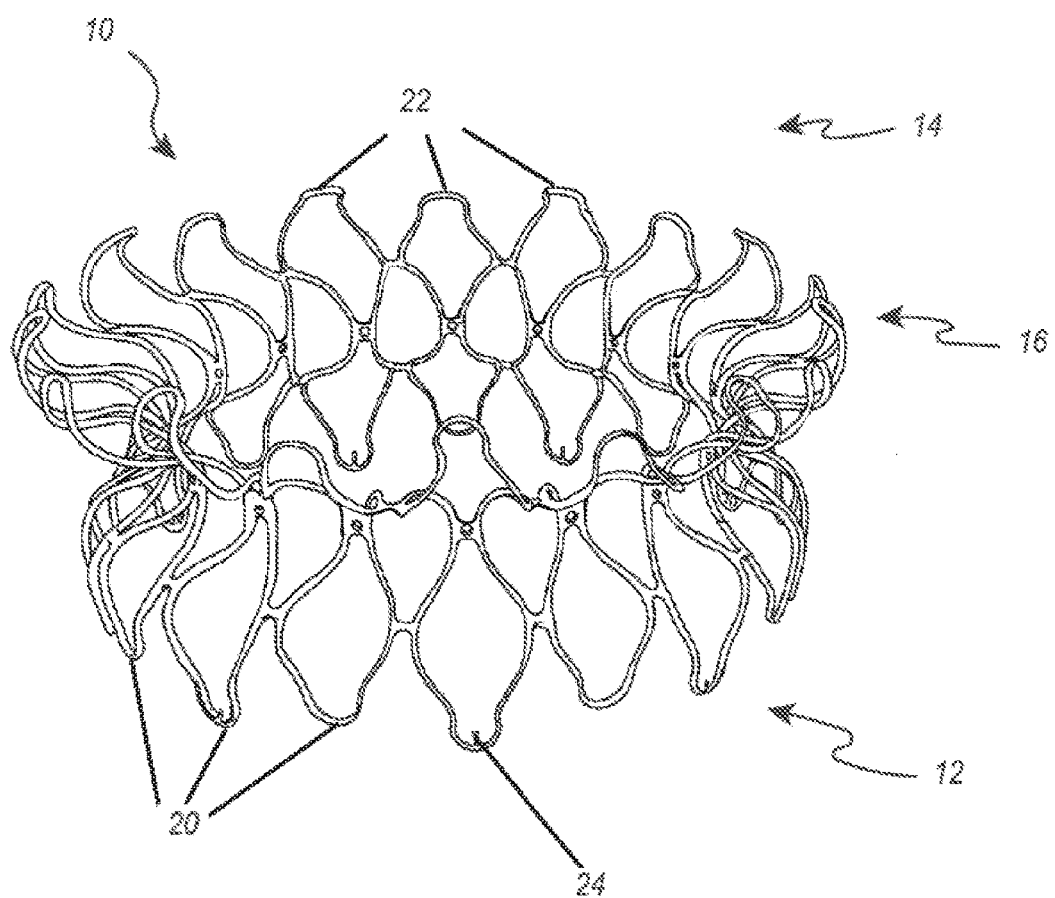
FIG. 4 is a perspective view of one embodiment of an artificial heart valve.

FIG. 4 shows one example of a replacement heart valve device that can be intravascularly delivered and deployed using the devices, systems, and methods disclosed herein. It should be emphasized, however, that the depicted replacement valve is only one example, and the devices, systems, and methods disclosed herein can be adapted to work with a variety of alternative implantable devices of differing shapes and sizes. In the embodiment illustrated in FIG. 4, valve 10 can be configured to self-expand within a cardiac valve orifice, such as the mitral annulus, so that the central portion lines the valve orifice while the atrial and ventricular anchors sit within the chambers of the heart and pinch tissue of the orifice therebetween, securing the valve in place within the heart.

The valve can include an expandable anchor that includes an atrial anchor or ring 12, a ventricular anchor or ring 14, and a central portion 16 disposed axially between the atrial anchor 12 and the ventricular anchor 14. The atrial anchor 12 can be configured to be placed on, and to engage tissue adjacent to, the atrial side of a mitral annulus. Similarly, the ventricular anchor 14 can be configured to be placed on, and to engage tissue adjacent to, the ventricular side of a mitral annulus. The valve 10 can be formed of a shape-memory alloy adapted to be collapsed into a collapsed delivery configuration (by the application of external forces) and biased to return to and expand into an expanded configuration. The valve 10 can also include a plurality of struts secured to at least one of the atrial anchor 12, the ventricular anchor 14, or the central portion 16, the struts being secured to a plurality of replacement leaflets or crests.

The strut frame can be cut from a tubular element, then expanded, and set in the expanded configuration using known shape setting techniques. For example, in an exemplary embodiment, the frame can be cut from a 10 mm diameter tube, then expanded to an expanded configuration of about 32 mm, and set in the expanded configuration. In some exemplary embodiments the strut frames herein are 0.25 mm to about 0.45 mm thick, such as about 0.35 mm thick. The annular strut frame can be cut from a flat sheet and rolled up and secured together or it can be cut from a tubular structure.

As further illustrated in FIG. 4, the atrial anchor or ring 12 can be formed from a plurality of atrial leaflets or crests 20 that can be radially spaced about the periphery of the valve 10 and that, in an expanded configuration, extend proximally and radially outward from a proximal end of the central portion 16. Similarly, the ventricular anchor or ring 14 can also be formed from a plurality of ventricular leaflets or crests 22 that can be radially spaced about the periphery of the valve 10 and that, in an expanded configuration, extend distally and radially outward from a distal end of the central portion 16.

Figure 5:
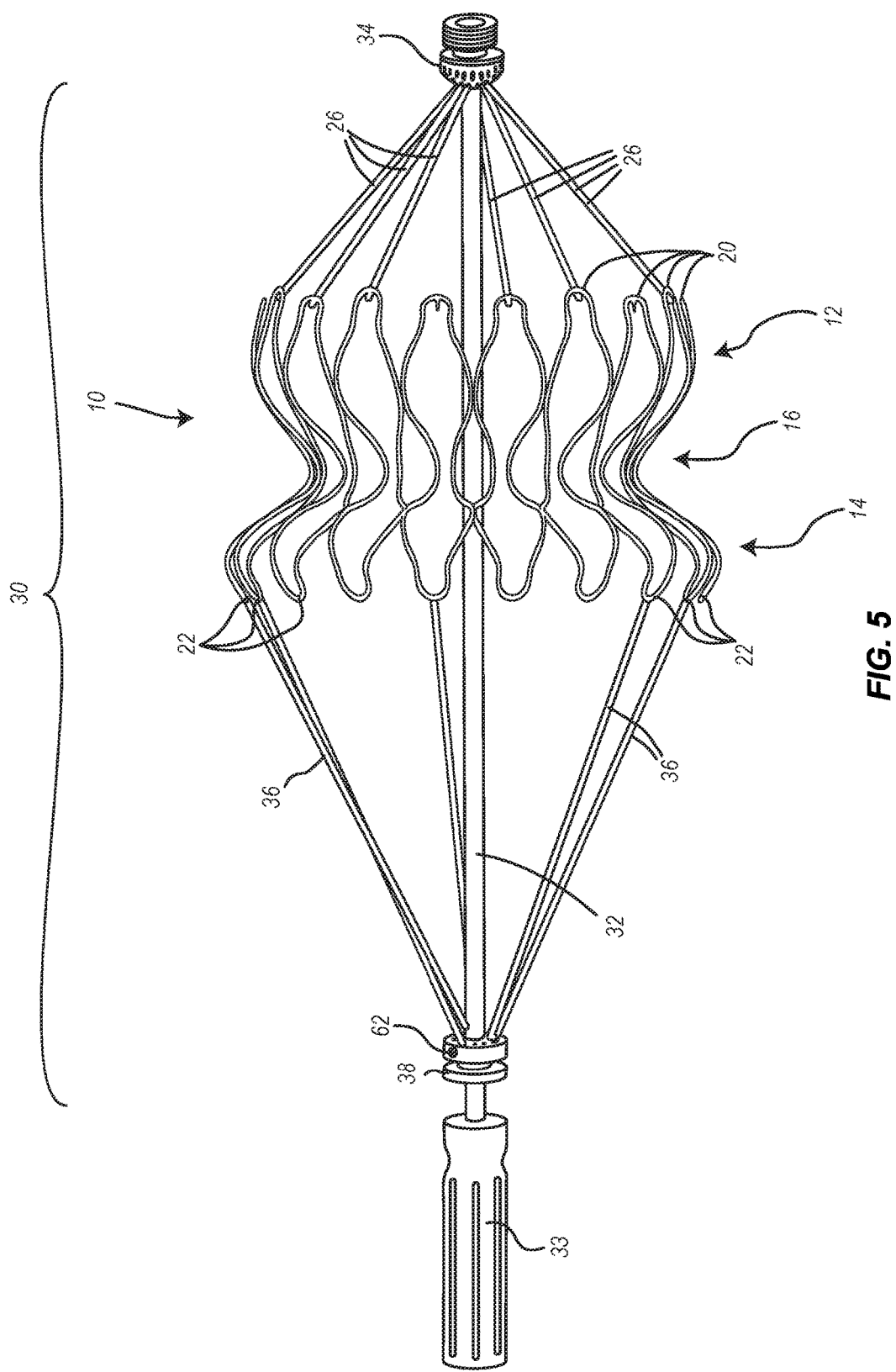
FIG. 5 is a perspective view of an embodiment of a heart valve assembly.
Figure 7:
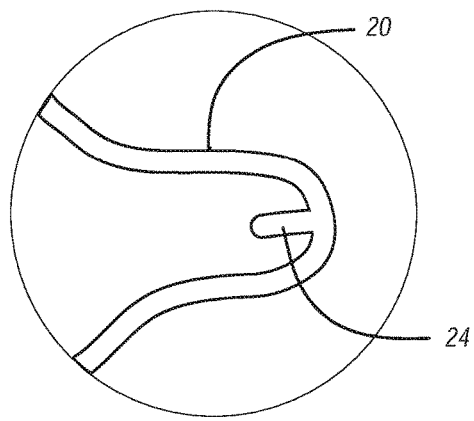
FIG. 7 is a detail view of one of the crests of the heart valve of FIG. 4, showing an embodiment of a pin for connecting suture loops to the heart valve.

As shown in FIGS. 4, 5, and 7, the valve 10 can also include attachment members 24 to which suture loops can be secured. These attachment members 24 can be straight hooks, straight pins, I-connectors, or other structures extending from a strut or member of the valve and to which a suture loop can be securely connected during delivery, positioning and deployment of the valve via a delivery catheter. At the same time, however, the size and configuration of the attachment members 24 should also be selected so as to facilitate a predictable, reliable and complete release of the sutures from the valve once the valve has been deployed and properly positioned within the target location.

In the illustrated embodiment, and as shown in greater detail in FIG. 7, the attachment members can take the form of a pin 24 provided at the apex of each atrial crest 20. Similarly, a pin 24 can be provided in some or all of the ventricular crests 22. In one embodiment, each pin 24 can be approximately 0.5 mm to approximately 2.0 mm in length and, preferably, can be approximately 1.0 mm-1.5 mm in length. Each pin 24 can also be bent slightly inwards towards a central axis of the valve 10.

As illustrated in FIG. 5, a distal end of a suture loop 26 can be passed around the outside of the atrial crest 20, passed over the end of the pin 24, and then drawn down to the base of the pin 24 by applying tension to the other, proximal end of the suture loop 26, thereby securing the distal end of the suture loop 26 between the base of the pin 24 and the inner surfaces of the apex of the atrial crest 20. With this configuration, tension on the suture loops 26 applied in a proximal direction will prevent unintended or inadvertent disconnection or release of each suture loop 26 from its associated pin 24. Once the valve 10 has been properly deployed and positioned within the target location, then release of the valve 10 can be achieved by removing tension on the suture loops 26, which allows the suture loops 26 to relax, detach from the pins 24 and, thereby, disconnect the delivery system from the valve 10. Valve 10 may also include a biocompatible fabric, mesh or other covering (not shown) over some or all of its exterior surface. If a such a covering is provided, gaps in the covering around each pin 24 can be provided so as not to interfere with the attachment of the suture loops 26 to pins 24 during assembly and/or release of suture loops 26 from pins 24 following deployment.

It should be appreciated that the process of threading a plurality of suture loops 26 around and onto the connecting pins 24 could be a relatively difficult, time consuming and tedious task if attempted in the lab just prior to a procedure. To provide a more convenient means for connecting a plurality of discrete suture loops between the valve and a delivery system, the other end of the suture loops 26 can be connected to a connecting ring 34, which can be biased to maintain tension on the suture loops 26. The connecting ring can also include a fastener or other suitable connection means formed at its proximal end that can be selectively coupled to a complementary fastener or other suitable connection means formed at the distal end of the delivery system.

Figure 6:
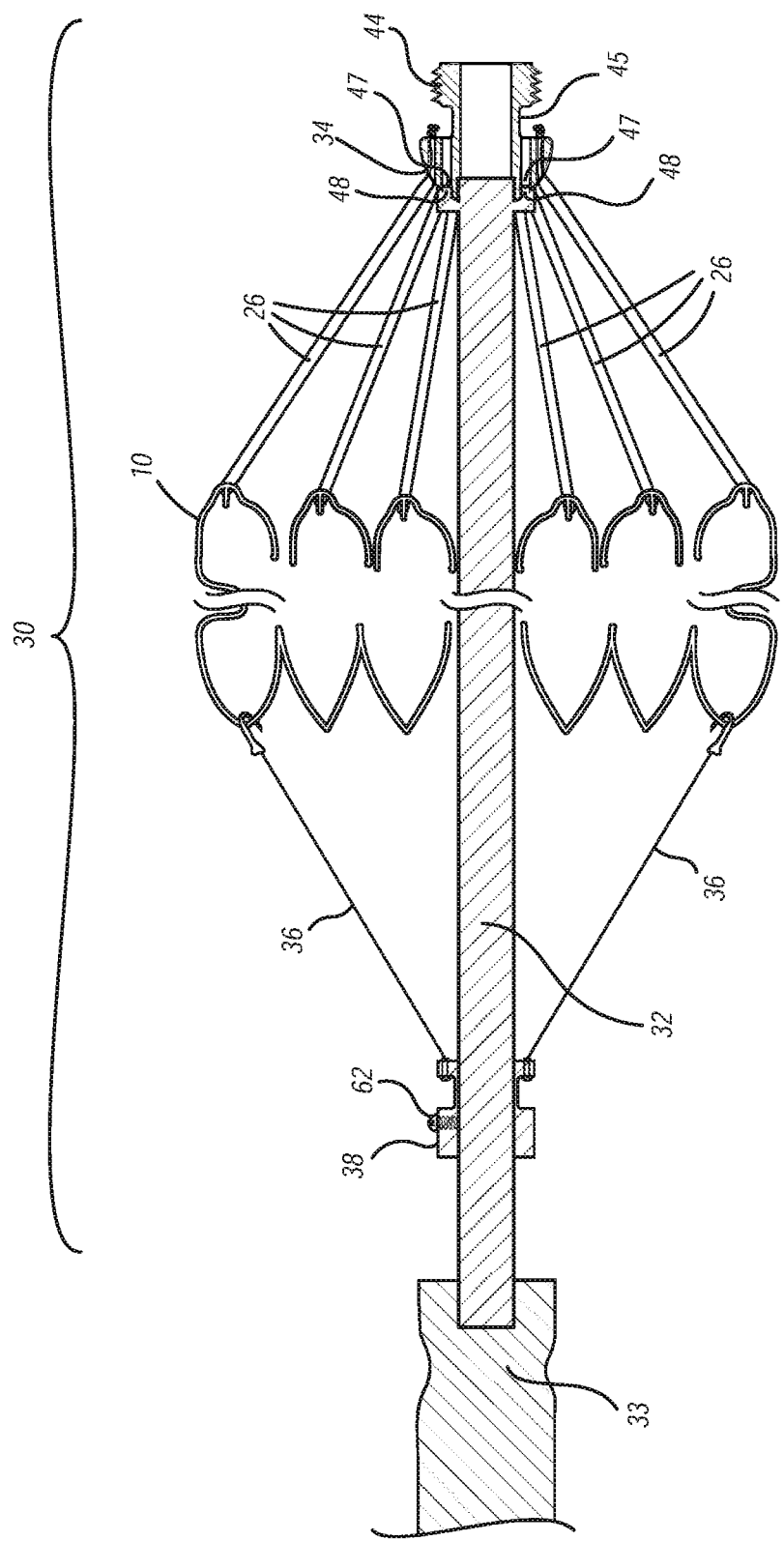
FIG. 6 is a cross-sectional view of the heart valve assembly shown in FIG. 5.

Referring to FIGS. 5 and 6, which illustrate a heart valve assembly that can be pre-assembled and packaged in a suitable sterile solution, such as glutaraldehyde, and which also provides a convenient mechanism for easily attaching the heart valve assembly to a delivery system. In one embodiment, the heart valve assembly 30 can include valve 10, a plurality of suture loops 26, an elongate shaft or mandrel 32, a connecting ring 34, a plurality of sacrificial sutures 36, and a sacrificial suture ring 38. Elongate shaft 32 extends longitudinally through the center of the central portion 16 of valve 10, extends proximally beyond a proximal end of the valve 10 and extends distally beyond a distal end of valve 10.

Figure 8A:
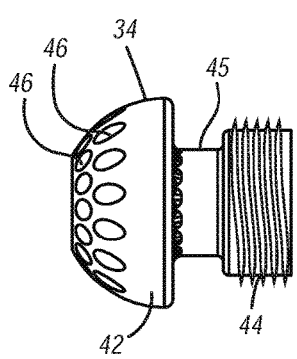
FIGS. 8A through 8C illustrate side, cross-sectional, and perspective views, respectively, of an embodiment of a connecting ring of the heart valve assembly.
Figure 8B:
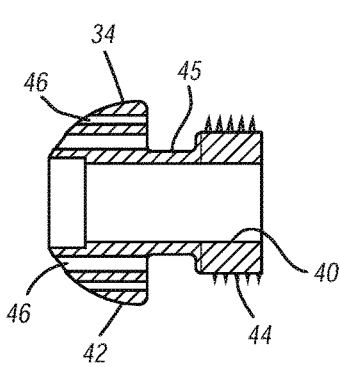
Figure 8C:
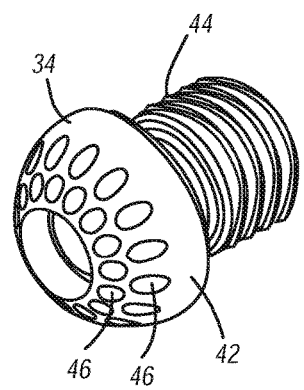
Figure 9A:
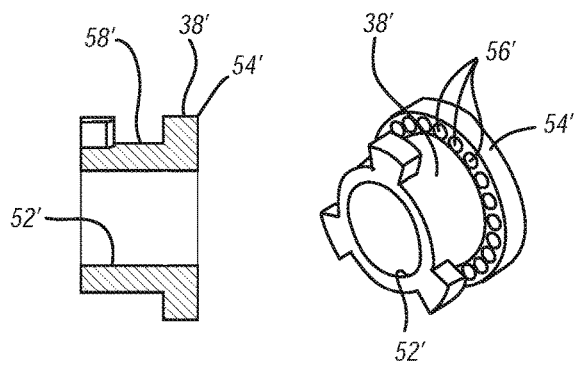
FIGS. 9A and 9B illustrate cross-sectional and perspective views, respectively, of another embodiment of a connecting ring of the heart valve assembly.
Figure 9B:
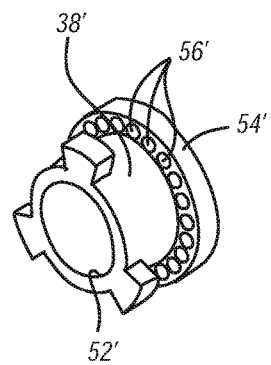

Connecting ring 34 is positioned adjacent and engages a proximal end of elongate shaft 32. FIGS. 8A through 8C provide detailed views of one embodiment of connecting ring 34. In the illustrated embodiment, the connecting ring 34 can include a center lumen 40, a distal shoulder portion 42, and a proximal threaded portion 44. Distal shoulder portion 42 includes a plurality of holes 46 spaced radially about the periphery thereof, through which the distal end of suture loops 26 can be secured to connecting ring 34. Connecting ring 34 can also include an annular recess 45 separating the distal shoulder portion 42 and the proximal threaded portion 44. Annular recess 45 provides a space for the knots and loose ends of the sutures loops 26 to reside. As the name implies, threaded portion 44 can include threads which, as discussed in additional detail below, can engage complementary threads formed in a distal end of a portion of the delivery system to connect the connecting ring 34 (and, thus, the heart valve assembly 30) to the delivery system. While the illustrated embodiment shows the use of threads to connect the connecting ring 34 to the delivery system, any other suitable type of complementary mechanically connection could be adapted and substituted for the threaded portions. For example, FIGS. 9A and 9B illustrate another embodiment of connecting ring 34' with a mechanical interlock as an alternative to the threaded connection shown in FIGS. 8A-8C. As shown in FIGS. 9A and 9B, connecting ring 34' can include a plurality of radially spaced apart extending members. These radially extending members can be configured to engage with a complementary structure within the distal end of a portion of the delivery system. For example, the distal end portion of the delivery system can include complementary slots or recess that receive the radially extending members in a friction fit or other mechanical manner through rotational positioning of the connecting ring relative to the delivery system, or vice versa.

The foregoing are two examples of means for selectively coupling the proximal end of heart valve assembly 30 to a distal end of a delivery system. It should be understood, however, that the phrase "means for selectively coupling the proximal end of heart valve assembly 30 to a distal end of a delivery system" is intended to also encompass other elements, structures and configurations that are known in the art and that can be substituted and used to perform the same function.

As illustrated in FIG. 6, connecting ring 34 can also include two or more recesses 47 formed in its distal face that are configured to receive corresponding pins 48 that can be provided in the proximal end of mandrel 32. The selective coupling of pins 48 within recesses 47 fixes the rotational positions of mandrel 32 to connecting ring 34 to one another so that a user can selectively rotate mandrel 32 and connecting ring 34 together in a clockwise or counterclockwise direction. Mandrel 32 can also include a centering pin 49 that is sized to engage the center lumen 40 of connecting ring 34.

Located adjacent the distal end of elongate shaft 32 is a sacrificial suture ring 38. FIGS. 10A and 10B provide detailed views of one embodiment of sacrificial suture ring 38. In the illustrated embodiment, sacrificial suture ring 38 can include a center lumen 52 for receiving elongate shaft 32 therethrough. Sacrificial suture ring 38 can also include an annular flange 54 formed at its proximal end, with a plurality of holes 56 radially spaced about its periphery. Sacrificial suture ring 38 can also include an annular recess 58 in which suture knots and ends can be positioned. Sacrificial suture ring 38 can also include a hole 60 that extends radially outward from the central lumen 52, that is threaded, and that is configured to receive a set screw 62 therethrough for securing sacrificial suture ring 50 to elongate shaft 32. A plurality of sacrificial sutures 36 can be secured between pins 24 in the ventricular crests 22 of the valve 10 (see also FIGS. 5 and 6) and the holes 56 provided in the annular flange 54 of sacrificial suture ring 50. A desired amount of tension can be applied simultaneously to both the suture loops 26 and sacrificial sutures 36 by adjusting the position of sacrificial suture ring 50 along elongate shaft 32. Once the desired tension is achieved, then the position of the sacrificial suture ring 38 can be fixed by advancing set screw 62 into contact with elongate shaft 32, and the applied tension will prevent inadvertent or unintended release or separation of the suture loops 26 from the valve 10. Thus assembled, the heart valve assembly 30 can be packaged in a sterilized package or container suitable for storage and shipping. The package or container can also include a suitable sterile solution, such as glutaraldehyde.

While reference is made to use of "sutures" for suture loops 26 and sacrificial sutures 36, it should be understood that any elongate member that can provide the functions of the "sutures" described herein could substituted and used in place of sutures. For instance, other elongate members can provide a connection between two or more components or structures and can transmit forces, be tensioned, and be selectively disconnected from the two or more components or structures. As such, other materials, such as threads, wires, cords, ribbons, fibers, filaments, strands, cables, etc., or other suitable tensioning elements or members can be substitute and used in place of sutures.

In addition, while the connection between the distal end of valve 10 and the sacrificial suture ring 38 in one embodiment can comprise "suture loops," other configurations and also be used. For example, as shown in FIG. 6, sacrificial sutures 36 can each also comprise a single strand of suture tied at one end to the sacrificial suture ring 38 and fastened at the other end to a hook that can be selectively connected to and/or disconnected from the crests 22 of the ventricular ring 14.

Elongate shaft or mandrel 32 can also include a handle 33, similar to a screwdriver handle or other suitable configuration that can be selectively connected to or integrated as part of the distal end of shaft 32. Handle 33 can assist in handling and manipulating heart valve assembly 30, particularly while aligning and engaging the threads 44 of connecting ring 34 to the threads of the delivery system as described in additional detail below.

Figure 11:
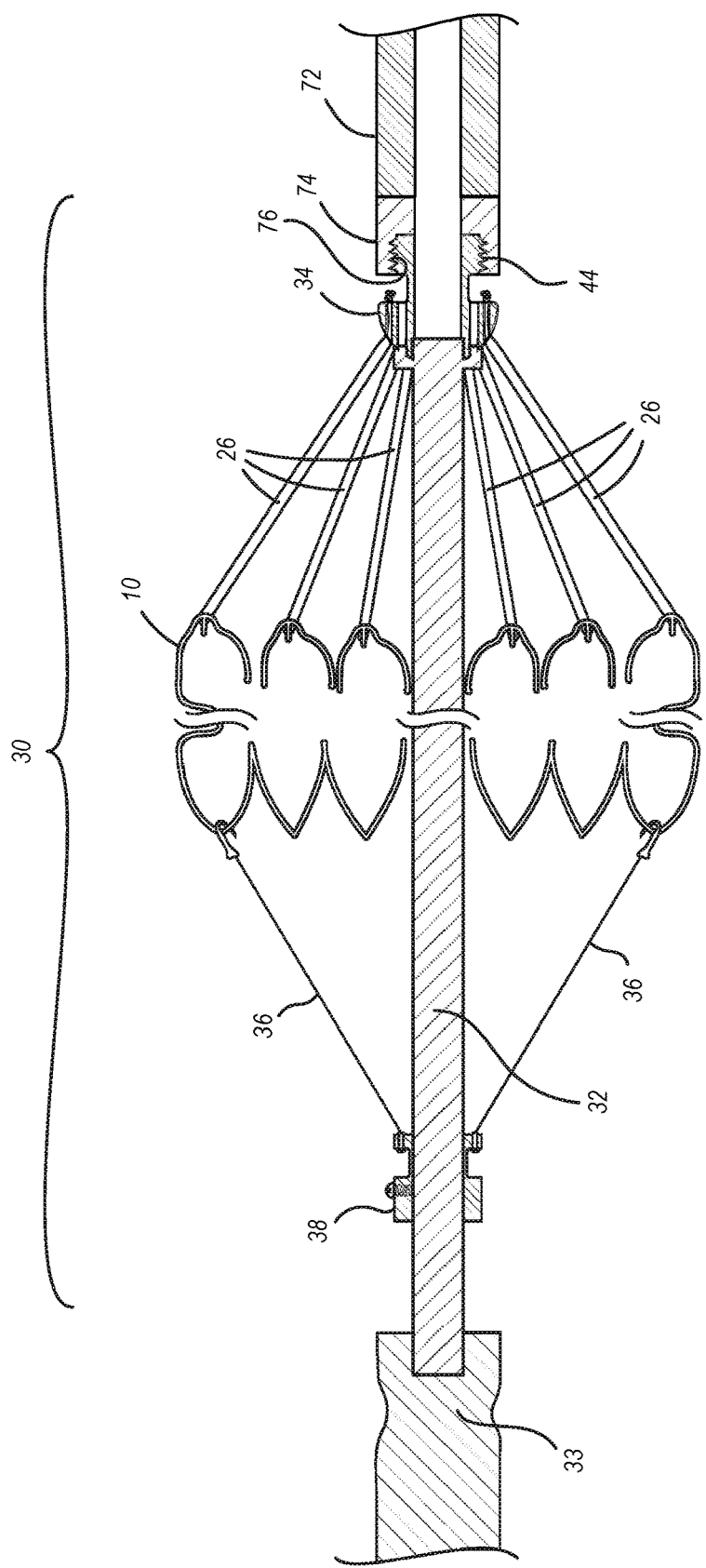
FIG. 11 is a cross-sectional view showing the heart valve assembly connected to a distal end of an embodiment of a delivery catheter.
Figure 12:
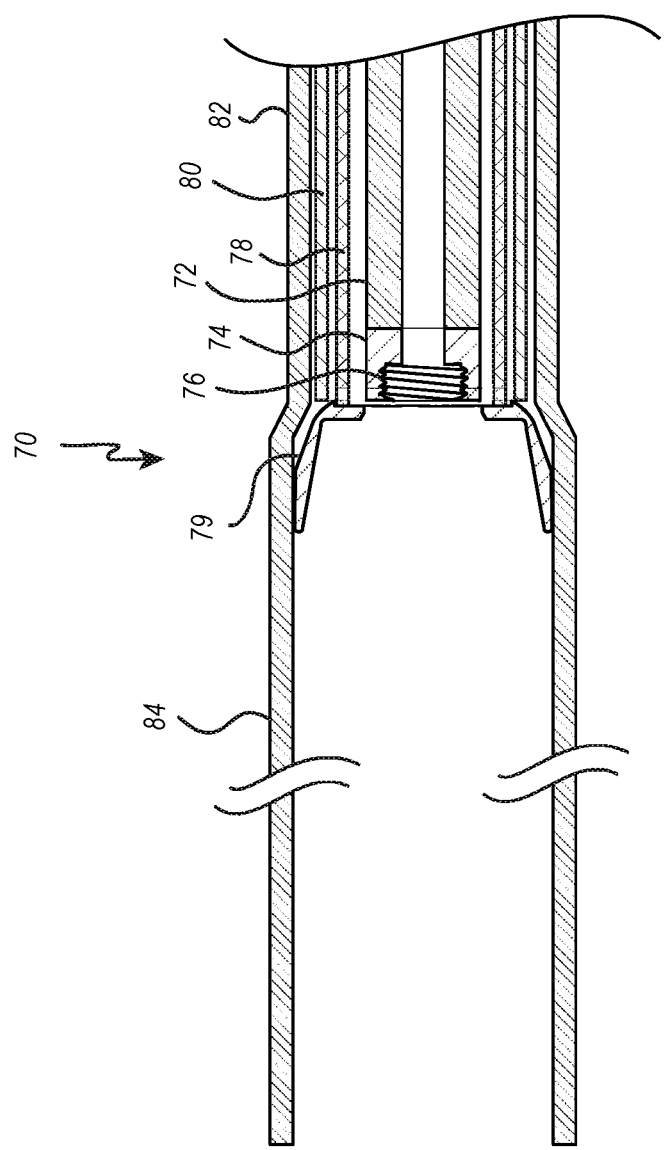
FIG. 12 is a cross-sectional view of a distal end portion of an embodiment of a delivery system for the heart valve.

Referring next to FIG. 11, as previously indicated, the proximal end of connecting ring 34, and thus the proximal end of heart valve assembly 30, can include a threaded portion 44 that is configured to selectively mate in threaded engagement with a complementary threaded portion of a delivery system. A portion of the distal end of the delivery member 70 is graphically represented in FIG. 12, showing the suture catheter 72 extending and terminating at a suture catheter tip ring 74. Suture catheter tip ring 74 can include a threaded portion 76 configured to selectively mate in threaded engagement with threaded portion 44 of the connecting ring 34 of the heart valve assembly 10 as illustrated. As previously mentioned, other suitable elements, structures and configurations can be used, in place of threads, to provide for selective coupling and decoupling between heart valve assembly 30 and delivery member 70. Due to the force that can be required to collapse the heart valve from its expanded configuration to a collapsed configuration, suture catheter 72 can preferably be made from a high tensile strength material capable of withstanding tension forces of up to 50 pounds (222.4 Newtons).

As graphically illustrated in FIG. 12, the delivery system 70 can also include other elements or layers that extend from the proximal end to the distal end. In some embodiments, at least one of the elements of the delivery system may be located radially and/or co-axially within an outer delivery sheath 82. In one embodiment, delivery system 70 can include a suture catheter 72, a delivery catheter 78, a steering catheter 80, an outer sheath 82, and/or a valve cover 84 positioned at the distal end of the outer sheath 82. The delivery system 70 can also include a guidewire lumen (not shown) positioned within the lumen of the suture catheter 72 and a guidewire (not shown) positioned within and extending through the lumen of the guidewire lumen. The various layers making up delivery system 70 may sometimes be collectively or generically referred to herein as "component" layers/members of the delivery system 70.

Delivery catheter 78 can consist of a stacked coil capable of selectively delivering a force in the distal direction sufficient to deploy heart valve 10 from valve cover 84. As previously mentioned, to overcome the frictional and other forces that can develop between the collapsed heart valve 10 and valve cover 84 (due to the resilience and spring force of the shape memory of heart valve 10), in some embodiments it may be necessary for the stacked coil of delivery catheter 78 to deliver a distal force of up to approximately 50 pounds (222.4 Newtons) in order to cause heart valve 10 to deploy from the distal end of valve cover 84. Delivery catheter 78 can also terminate in a distal end cap or can 79 (also shown as can 610 in FIG. 2) that engages the proximal ends of heart valve 10.

The delivery system 70 can also include, at its proximal end, a control fixture (not shown) that attaches to the proximal ends of the various component layers of the delivery system 70, and which can be used to manipulate and control movement of the various component layers of the delivery system 70 relative to one another to perform various functions, including loading the valve 10, navigating the delivery system 70 and valve 10 through the vasculature to a target location, positioning and deploying the valve 10 at the target site, and releasing the valve 10 from the delivery system 70.

In at least one embodiment, delivery member 70 can also include a friction-reducing layer and/or coating (not shown) on or between one or more component layers of delivery member 70. For example, a friction-reducing layer and/or coating may include a polytetrafluoroethylene (PTFE) layer positioned on the inner surface of outer sheath 82 and/or on the outer surface of steering catheter 80. In other examples, other lubricious coatings, such as perfluoroalkoxy (PFA), fluorinated ethylene propylene, other fluoropolymers, ceramic coatings, one or more materials combined with a polymer structure (such as PROPELL available from FOSTER CO.), other materials, or combinations thereof, may be applied to one or more component layers of delivery member 70 to reduce friction between the components/elements during movement relative to one another. In yet other examples, a hydrophilic or hydrophobic layer may be positioned on or between one or more of the component layers of the delivery member 70.

A replacement heart valve, such as valve 10, may be a self-expanding valve replacement device with a contracted or collapsed state or configuration and an expanded state or configuration. For example, valve 10 may be biased toward the expanded state or configuration such that the valve cover 84 holds the valve 10 in the contracted or collapsed state or configuration. By removing the valve 10 from the valve cover 84 (i.e., by moving the valve cover 84 in a longitudinal direction relative to the valve 10, or vice versa), valve 10 can be released from the valve cover 84 and allowed to expand from its contracted or collapsed state or configuration toward its expanded state or configuration. In some embodiments, valve 10 may include a shape memory material, such as a shape memory polymer and/or a shape-memory metal, such as a nickel titanium alloy.

As mentioned above, the heart valve assembly 30 can be preassembled in the manner described above and packaged in a sterile package or container suitable for transportation and storage. Prior to a procedure, the heart valve assembly 30 can be removed from its packaging or container and rinsed with saline solution. Then, the heart valve assembly 30 can be used to load the valve 10 into delivery member 70.

Figure 13:
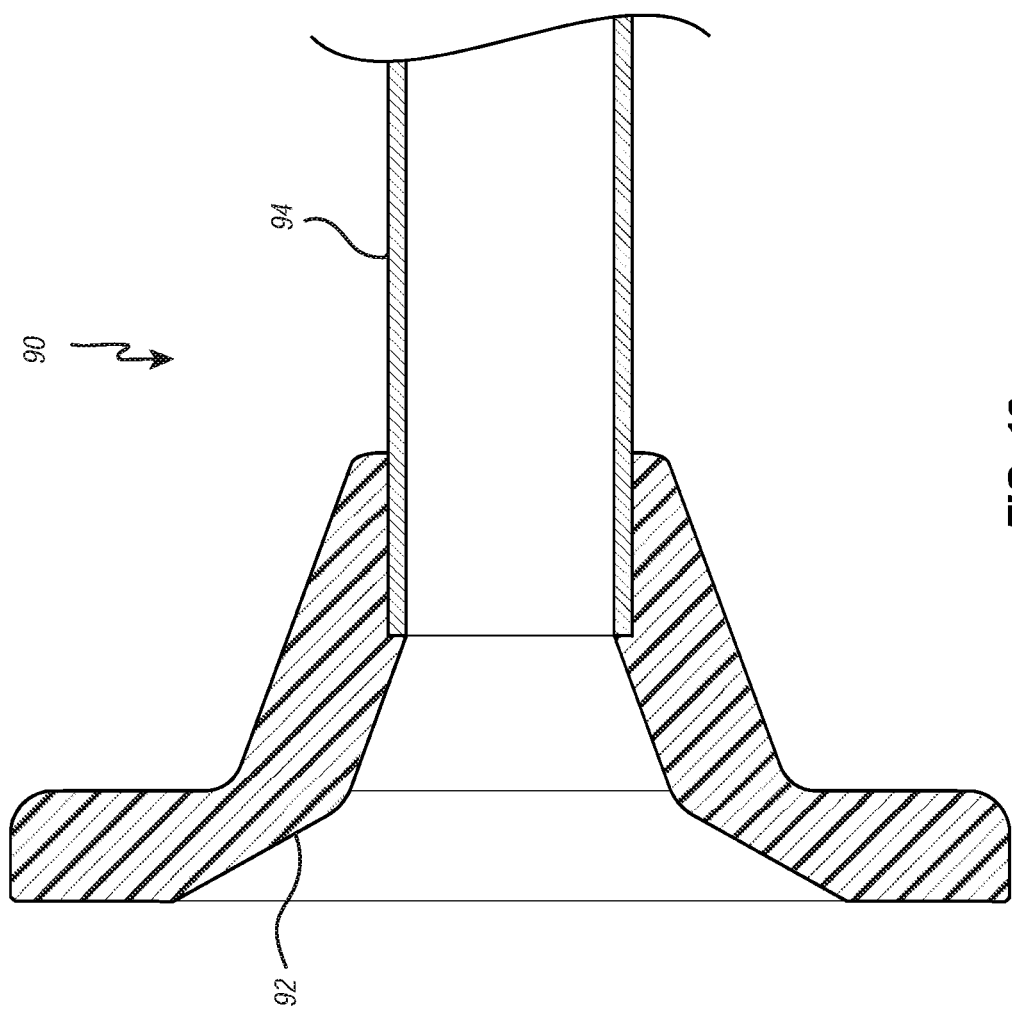
FIG. 13 is a cross-sectional view of an embodiment of a loading funnel used to collapse and load the heart valve into the delivery system.
Figure 14:
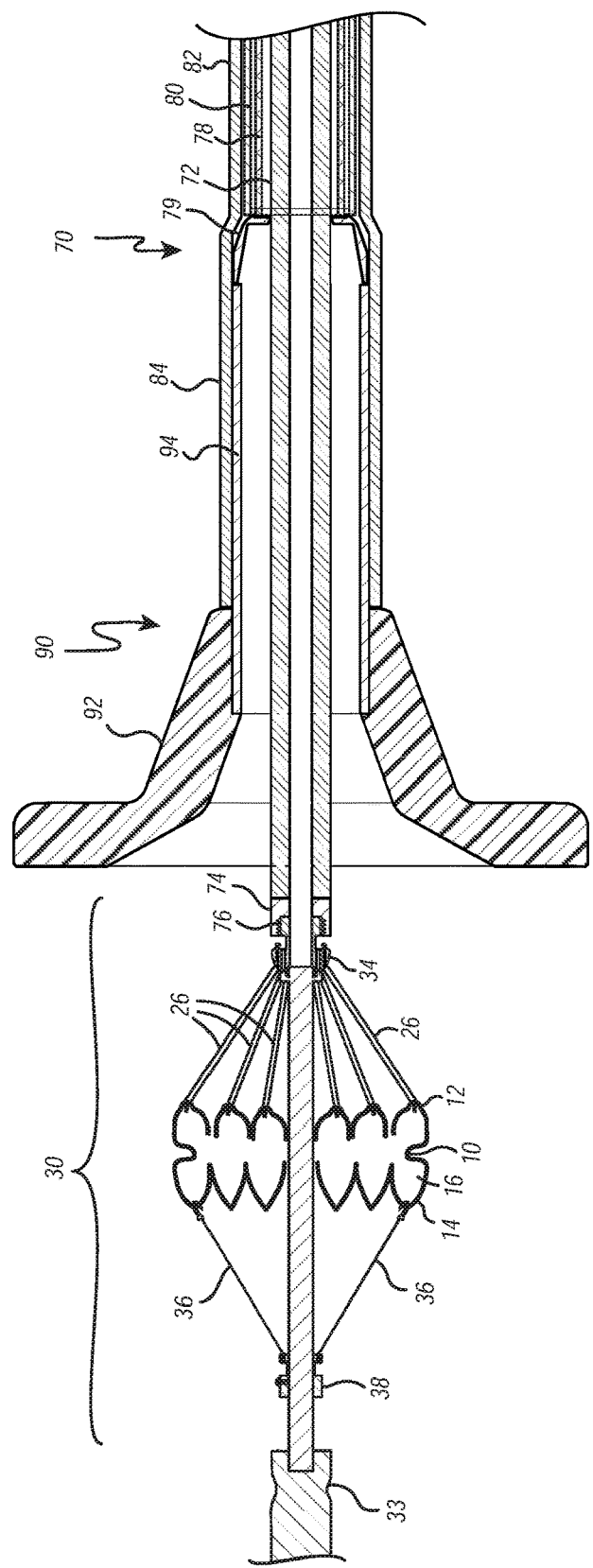
FIGS. 14 through 16 are cross-sectional views illustrating the heart valve being loaded directly into the delivery system.

Reference is next made to FIGS. 13 through 16, which illustrate one way in which the valve 10 can be collapsed and loaded into the valve cover 84 of the delivery member 70. First, FIG. 13 illustrates a loading funnel 90 that can be used to facilitate loading of the valve 10 into the valve cover 84 of delivery member 70. Loading funnel 90 can include a funnel portion 92 located at its distal end and an elongate tubular portion 94 located at its proximal end and communicating with the funnel portion 92. As shown, the funnel portion 92 can preferably be fashioned to smoothly transition from a large diameter at its distal end to a small diameter at is proximal end. The dimension of the large diameter of the funnel portion can preferably be larger than the outer diameter of the valve 10 in its expanded state, and the dimension of the small diameter of the funnel portion can preferably be approximately the same as the inner diameter of the tubular portion 94. The outer diameter of the tubular portion 94 can preferably be slightly smaller than the inner diameter of the valve cover 84 of the delivery member 70, and the tubular portion 94 can preferably be approximately the same length as the length of the valve cover 84 of the delivery member 70, such that the tubular portion 94 can be selectively inserted into and nest within the valve cover 84 of the delivery member 70, as illustrated in FIG. 14.

Figure 15:
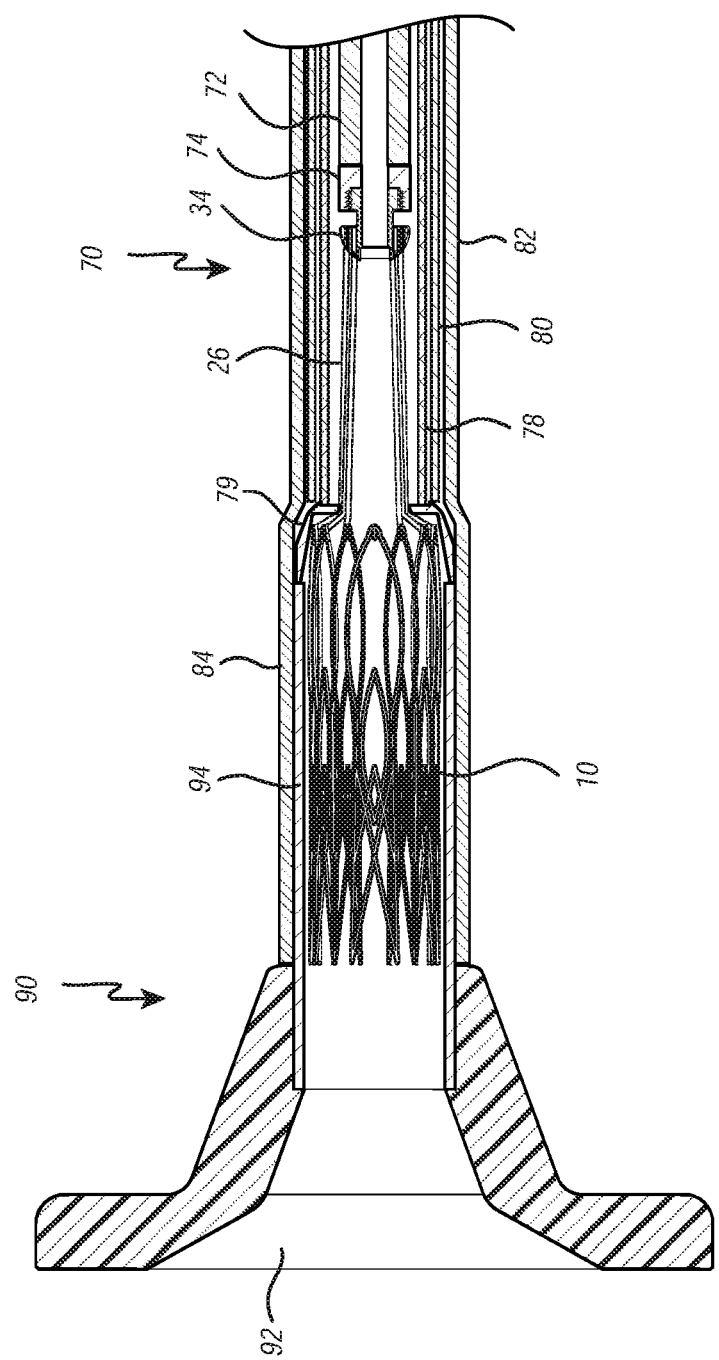
Figure 16:
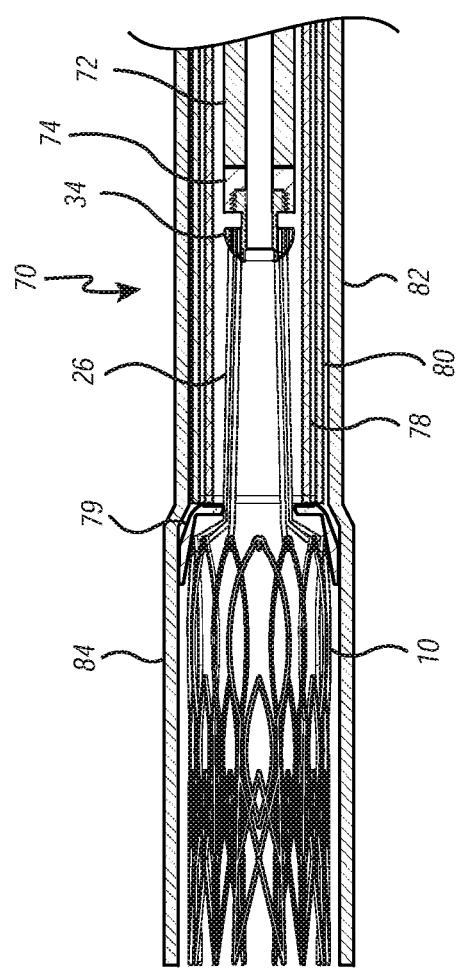

With the tubular portion 94 of the loading funnel 90 positioned within the valve cover 84, controls located on the control fixture (not shown) can be manipulated to cause the suture catheter 72 of the delivery member 70 to advance in a distal direction relative to the other component layers of the delivery member 70 until the tip ring 74 of the suture catheter 72 extends distally beyond the distal end of the tubular portion 94 and into the interior of the funnel portion 92, as shown in FIG. 14. Then, as also shown in FIG. 14, the threaded portion 44 of heart valve assembly 30 can be threaded into the threaded portion 76 of the tip ring 74 at the distal end of the suture catheter 72. Appropriate control knobs of the control fixture (not shown) can then be manipulated to retract the suture catheter 72 in a proximal direction relative to all of the other component layers of the delivery system 72 (and the loading funnel 90). As proximal movement continues, the suture loops 26 are drawn into the central lumen of the tubular member 94. This, in combination with the sloping walls of the funnel portion 92, cause the atrial crests 20 of the atrial disc 12 to collapse toward the central axis and, eventually, to enter the central lumen of the tubular portion 92. Once a sufficient amount of proximally-directed tension is placed on the suture loops 26 by the suture catheter 72, the sacrificial sutures 36 can be cut or otherwise separated from the ventricular ring 14 of the valve 10, and the elongate shaft 32, and the sacrificial suture ring 38 and the sacrificial sutures 36 can be withdrawn from the heart valve assembly 30 and set aside. Further proximal movement of the suture catheter 72 continues until valve 10 is completely collapsed and completely positioned within the tubular portion 94, as illustrated in FIG. 15. Then, the loading funnel 90 can be removed by sliding the loading funnel 90 in a distal direction relative to the delivery member 70. By maintaining tension on the suture catheter 72, the valve 10 remains stationary as the loading funnel 90 is withdrawn, leaving the fully collapsed valve 10 positioned completely within the valve cover 84 of the delivery member 70, as illustrated in FIG. 16.

Reference is next made to FIGS. 17 through 20, which illustrate another way in which the valve 10 can be collapsed and loaded into the valve cover 84 of the delivery member 70. Due to the material and structural properties of the valve 10, coupled with the relatively large diameter of valve 10 in its expanded state compared to the relatively small diameter of the valve cover 84, a relatively large force can be required to collapse valve 10 from its expanded state to a collapsed state and/or to draw the valve 10 into the valve cover 84. In some cases, a tension force of as much as 40 to 50 pounds (or 177.9 to 222.4 Newtons) may be required to collapse valve 10 and draw it into valve cover 84. To avoid the need to provide a delivery system capable of withstanding that much tension, a separate loading tool can also be provided that is capable of developing the tension needed to collapse and draw valve 10 into a sheath that is approximately the same size as the valve cover 84 and then transfer the collapsed valve 10 from the loading tool to the valve cover 84 of the delivery member 70.

Figure 17:
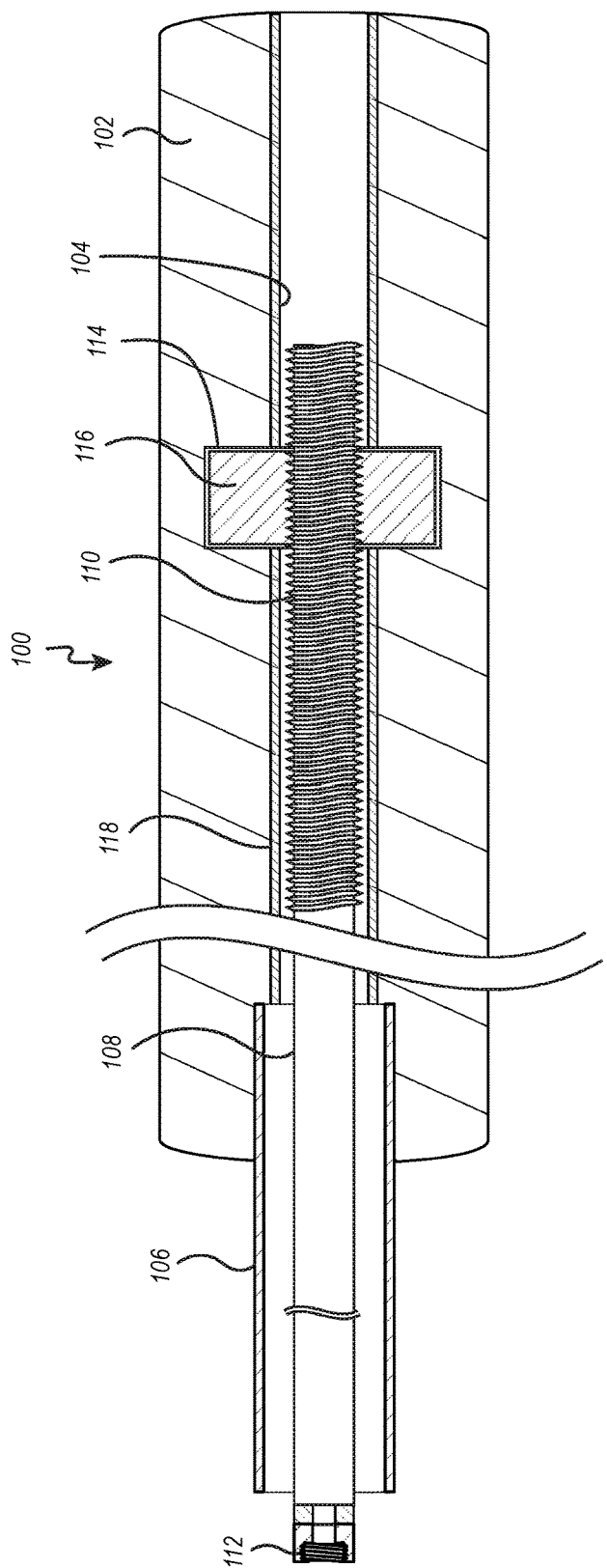
FIG. 17 is a cross-sectional view of an embodiment of a loading tool used to collapse and load the heart valve into a loading funnel.

In this embodiment, the valve 10 is loaded into the loading funnel 90 before the valve 10 is connected to the delivery member 70. To do this, a separate loading tool 100 can be provided, which is illustrated in FIG. 17. Loading tool 100 can include an elongate handle 102 with a lumen 104 that extends through the longitudinal axis of the handle. Located within lumen 104 is an elongate cylindrical sleeve 106 and an elongate shaft 108. Sleeve 106 and shaft 108 can be sized so that shaft 108 closely fits within the lumen of sleeve 106 and yet slides easily within sleeve 106. Shaft 108 can include a proximal threaded portion 110 on the outside of a portion of its proximal end. Shaft 108 can also include a distal threaded portion 112 located at its distal end. The threads of distal threaded portion 112 are complementary of, and are configured to engage the threads of proximal threaded portion 44 of the connecting ring 34 of the heart valve assembly 30 as discussed in additional detail below.

Handle 102 also includes a recess 114 that holds a thumbwheel 116. Thumbwheel 116 includes a central threaded bore 118 with threads that are complementary of the proximal threaded portion 110 of the shaft 108. By rotating thumbwheel 116 about the longitudinal axis of loading tool 100, the threads of thumbwheel 116 interact with the threads on shaft 108 to selectively advance or retract shaft 108 relative to handle 102, depending on the direction in which thumbwheel 116 is rotated. Loading tool 100 can also include a quick release feature (not shown) that allows selective engagement/disengagement of the cooperating threaded portions, as to allow shaft to be quickly advanced and retracted to a desired position relatively handle (and without having to do so rotating the thumbwheel 116 alone).

Figure 18:
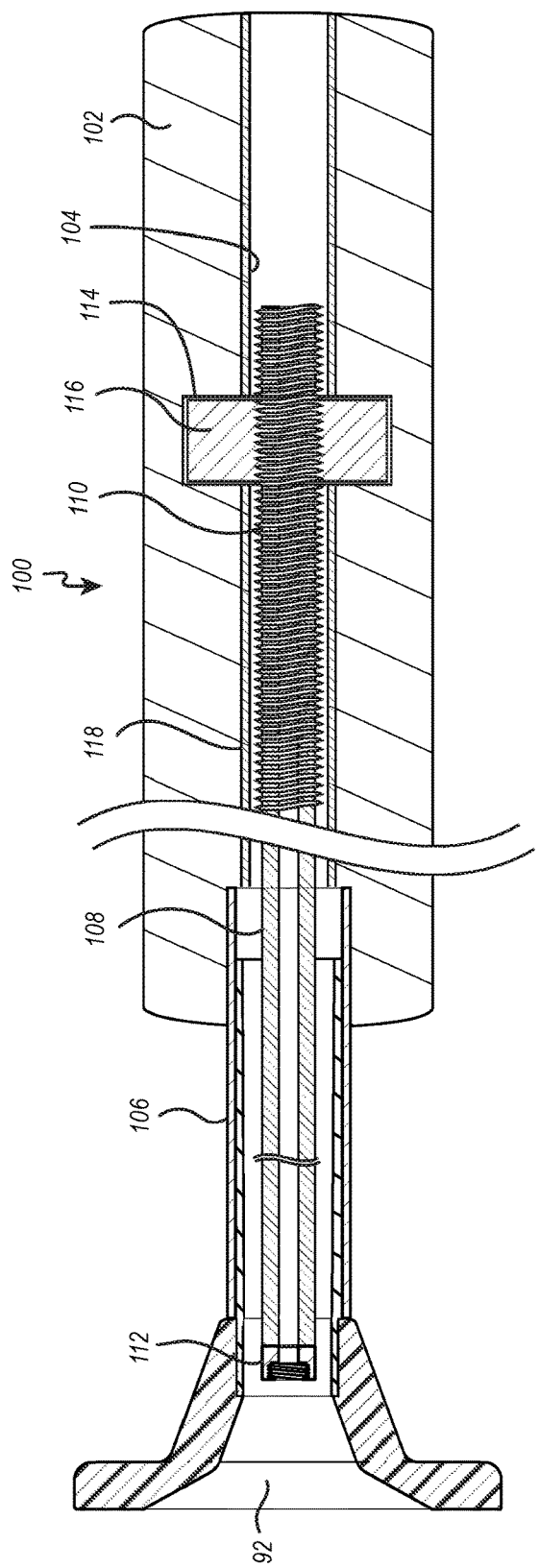
FIGS. 18 and 19 are cross sectional views illustrating the heart valve being loaded into a loading funnel with the use of the loading tool of FIG. 18.

Located at its distal end, the loading tool 100 also includes a hollow cylindrical tube 118 that is concentrically aligned with the central lumen 104 and that extends in a distal direction from the distal end of the handle 102. The inner diameter of the tube 118 can preferably be slightly larger than the outer diameter of the tubular portion 94 of the loading funnel 90, and the length of the tube 116 can preferably be approximately the same as the length of the tubular portion 94 of the loading funnel 90, such that the tubular portion 94 of the loading funnel 90 can be selective inserted into and nest within the tube 118, as illustrated in FIG. 18.

Figure 19:
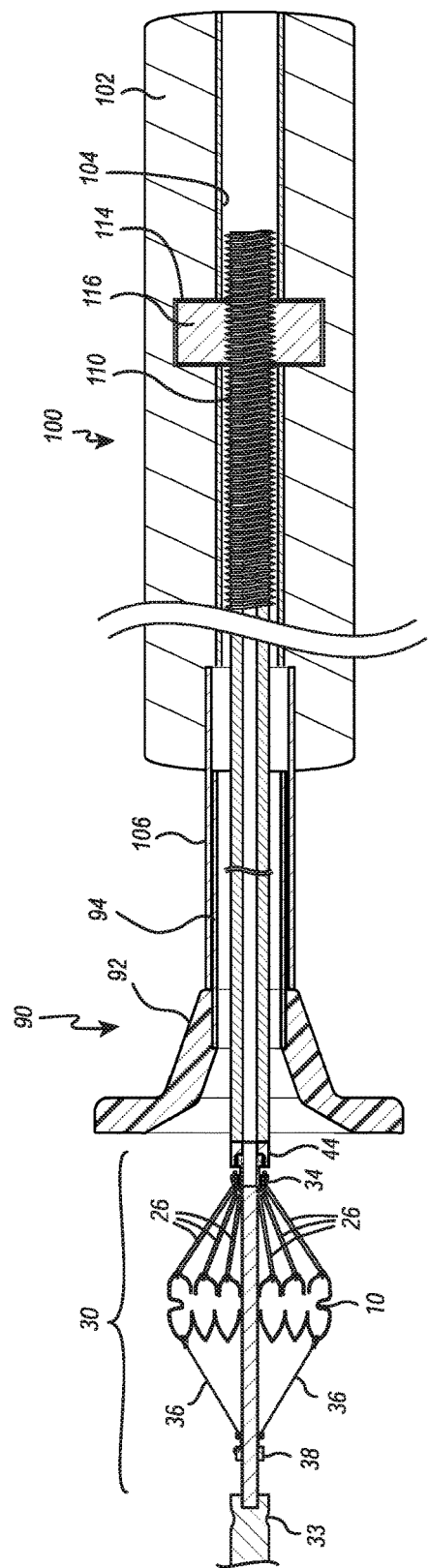

With the loading funnel 90 attached to the distal end of the loading tool 100, thumbwheel 116 can be rotated to advance shaft 108 in a distal direction until the distal threaded portion 112 of shaft 108 extends beyond the distal end of tube 118 and into the interior of the funnel portion 92, as shown in FIG. 19. Then, as also shown in FIG. 19, the threaded portion 44 of heart valve assembly 30 can be threaded into the distal threaded portion 112 of shaft 108 of the loading tool 100. Then, the thumbwheel 116 can rotated in the other direction to cause shaft 108 to move in a proximal direction, which causes the suture loops 26 into the tubular portion 94 of the loading funnel 90. Loading of the valve into the loading funnel continues in a manner similar to that described above, except that the loading handle 100 is used to draw the valve 10 into the loading funnel 90 instead of the suture catheter 72 of the delivery system.

Figure 20:
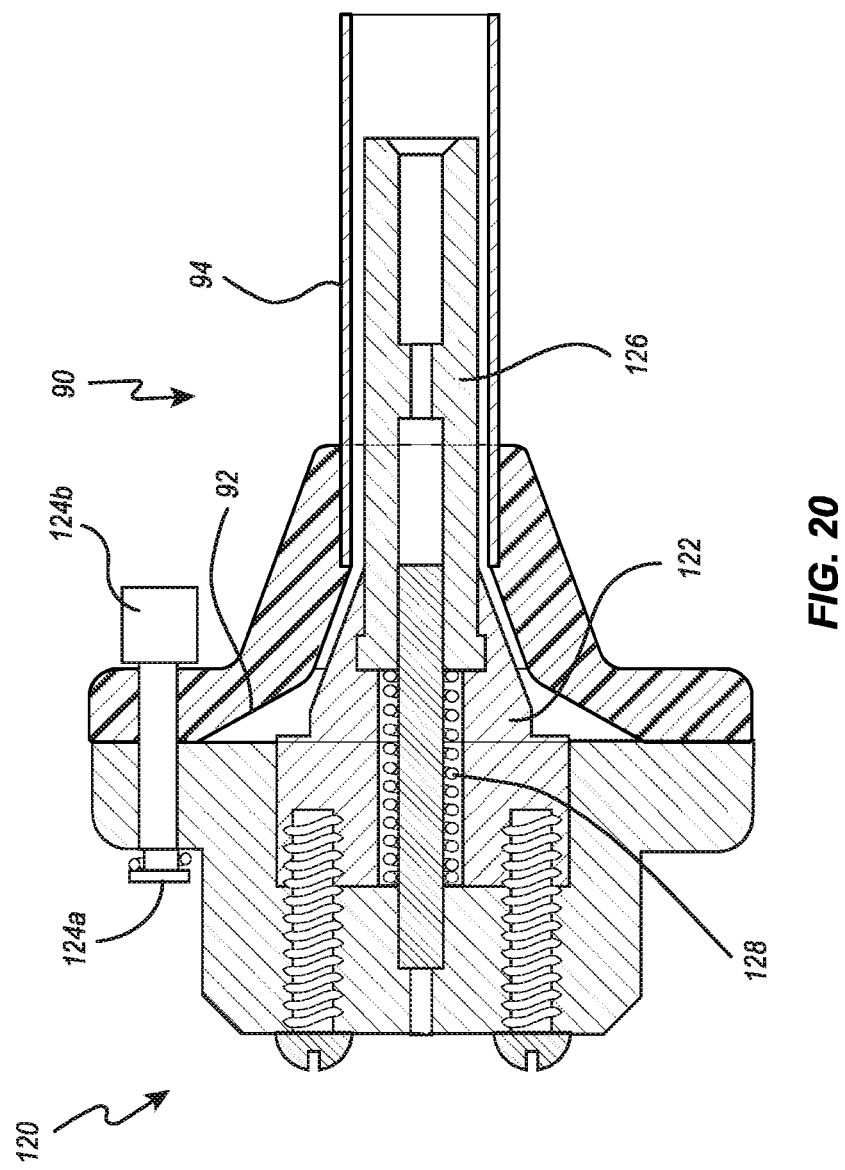
FIG. 20 is a cross-sectional view of an embodiment of a tensioning tool used to maintain sutures under tension while the collapsed heart valve is transferred from a loading funnel to a delivery system.

Once the valve 10 is fully collapsed and completely positioned within the tubular portion 94 of loading funnel 90, it is then necessary to disconnect connecting ring 34 from shaft 108 of the loading tool 100 and to then connect connecting ring 34 to the suture catheter tip ring 74 of the delivery member 70. Before doing so, however, a tensioning tool can be attached to the loading funnel 90, the tensioning tool being configured to ensure that suture loops 26 are maintained under tension during the time the collapsed valve assembly is being transferred from the loading tool 100 to the delivery member 70. One embodiment of such a tensioning tool 120 is illustrated in FIG. 20. Tensioning tool 120 can include a flared portion 122 that is generally complementary in shape to the interior region of the funnel portion 92 of loading funnel 90. As illustrated, loading funnel 90 and tensioning tool 120 can include complementary fasteners 124a and 124b that allow tensioning tool 120 to be selectively connected to and disconnected from loading funnel 90. Tensioning tool 120 also includes a spring biased plunger 126 that is biased in a proximal direction. The distal end of plunger engages a bias spring 128 positioned within a recess formed in the interior of the tensioning tool 120. When tensioning member 120 is attached to loading funnel, the force of bias spring 128 biases plunger 126 in a proximal direction and into engagement with a center portion of the connecting ring 34. This proximally-applied force presses against connecting ring 34, which places and maintains suture loops 26 under tension.

Once tensioning member 120 has been connected to loading funnel 90 (causing tension to be applied to suture loops 26 by spring biased plunger 126), then thumbwheel 116 can be rotated to cause shaft 108 to move in a distal direction until the connecting ring 34 emerges beyond the distal end of tube 118 of loading tool 100. At that point, connecting ring 34 can be disconnected from the distal thread of shaft 108 and can then be connected to the threaded portion of the suture catheter 72 of the delivery member 70 in a manner described above. Then, appropriate controls of the control fixture of delivery member 70 can be actuated to move suture catheter 72 in a proximal direction, thereby drawing the tubular portion (with the collapsed valve 10 contained therein) into the valve cover 84 of the delivery system. Then, with tension maintained on the suture loops 26 by means of the control fixture through the suture catheter 72, the loading funnel 90 and the tensioning tool 120 can be removed by sliding them in a distal direction relative to the valve cover 84.

To help reduce the forces needed to collapse and draw the valve 10 through the funnel portion 92 and into the tubular portion 94, once attached to the suture catheter 72, the heart valve assembly 30 and the loading funnel 90 can be placed in an ice and/or water bath to lower the temperature of the valve 10 and cause the shape memory alloy to "relax" and become more flexible. In addition, to help collapse the valve 10 in a more radially symmetric configuration, at various times during the loading process the valve 10 can be transferred from the ice/water bath to a warm/hot water bath and then back to the ice/water bath. The warm/hot water bath causes the valve 10 to flex as it attempts to return to expanded shape memory configuration (albeit portions of the valve 10 being constrained by the loading funnel 90). This flexing helps the valve 10 to "self-center" itself within the loading funnel 90 and helps valve 10 achieve a more symmetrical, collapsed configuration as loading continues. The valve 10 is then returned to the ice/water bath, and loading continues by continuing proximal movement of the suture catheter 72. The process of alternating between an ice/water bath and warm/hot water bath can be repeated one or more times, as needed, during the overall loading process.

The process of loading the valve 10 through loading funnel 90 and into valve cover 84 can be further assisted by providing a support fixture that combines a container for the ice/water bath and a clamping mechanism that securely holds the distal end of the delivery member 70, including valve cover 84, in a secure and stationary position during the loading process. For example, such a support fixture can include a water tight container capable of holding an ice/water bath in which heart valve assembly 10, loading funnel 90 and the distal end of delivery member 70 (i.e., valve cover 84) can be submerged. The support fixture can also include a clamp secured to the container and located below the "water line" of the ice/water bath. The clamp can be used to selectively clamp down on valve cover 84 to secure valve cover 84 in a fixed and stationary position during loading of valve 10 into valve cover 84.

Figure 21A:
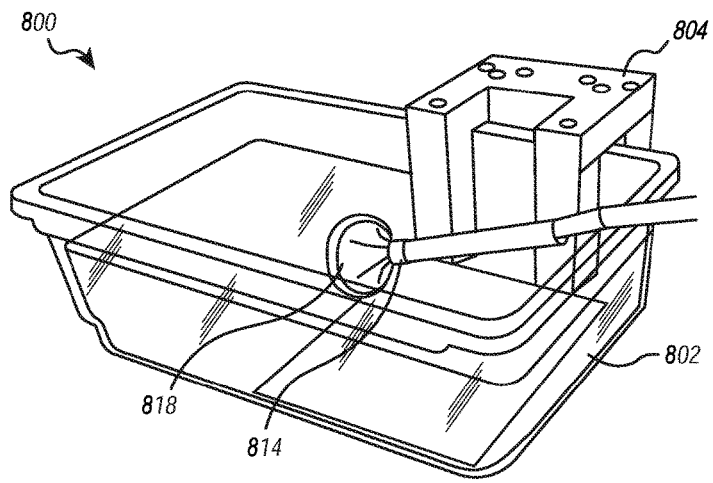
FIGS. 21A and 21B illustrate an embodiment of an assembly for loading a valve into the distal end of the delivery system.
Figure 21B:
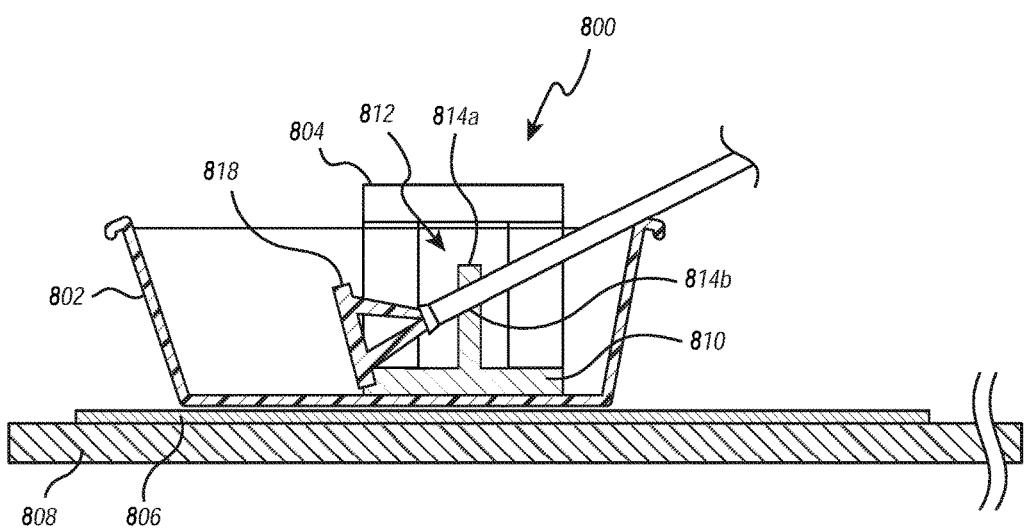

FIGS. 21A and 21B illustrate an embodiment of a support fixture/container. As illustrated, loading assembly 800 can include a reservoir 802 for holding an ice/water bath (other liquid) that can lower the temperature of the tissue valve, and in particular the frame or Nitinol structure, to below its martensite transformation temperature. By loading the valve when its temperature is below the martensite transformation temperature, the loading process occurs in a low temperature phase in which any plastic or elastic deformation influenced by the valve during loading does not affect the final expanded deployed state of the tissue valve. In other words, once the temperature of the valve returns above the martensite transformation temperature, the valve will transition to the austenite phase and to the deployed, expanded configuration. In addition, the effect on the Nitinol also reduces the forces needed to pull in the tissue valve into the outer sheath or valve cover.

As further illustrated, the loading assembly 800 can also include a fixture 804 that extends into an interior of the reservoir 802 on one side and mounts to a base member 806. Fixture 804 can transmit the forces to hold the valve cover to the base member 806 and then to a table or other support 808 that stabilizes the base member 806. Base member 806 and support 808 could be combined into a single support or structure for supporting reservoir 802 and one or more of the parts or portions of the loading assembly 800.

Fixture 804 can overlap a portion of reservoir 802 with a lower portion 810 submerged in the liquid. Lower portion 810 can be inclined to accommodate an angular orientation of outer sleeve or sheath or a portion of the elongate member. In another embodiment, lower portion 810 need not be inclined, but can be generally parallel to a bottom portion of the reservoir 802 or the base member 806.

Extending from lower portion 810 can be a clamping assembly 812 configured to receive and retain the outer sleeve, sheath, or valve cover relative to reservoir 802 and fixture 804. Clamping assembly 812 can include two half rings 814a and 814b that can be selectively connected by screws or other suitable fasteners. To simplify and speed up the procedure in a cath-lab, clamping assembly 812 can also include a quick engagement/release mechanism. For example, one side of each of the two half rings is pivotally mounted together and the other side includes a quick engagement/release lever and mechanism, such as an eccentric clamp or other toggle release. In another embodiment, a single half ring can be mounted to body 816 of the clamping assembly 812 that has formed therein a curved portion to receive the outer sleeve, sheath, or valve cover. In another embodiment, clamping assembly 812 can also be disposed outside of the reservoir 802, but mounted to the base member 806. In either embodiment, clamping assembly 812 securely supports and maintains the valve cover in a stationary position within the ice/water bath, while allowing axial movement of other component layers of the delivery system relative to the valve cover.

As further illustrated, loading assembly 800 can also include a guiding member 818 that guides the tissue valve into the valve cover or outer sheath. Guiding member 818 can be disposed on the end of the valve cover or outer sheath prior to attaching the valve to the delivery system. In another embodiment, guiding member 818 could be formed in two pieces that can be selectively coupled together, which would allow it to be placed around a portion of the valve cover or outer sheath after the intravascular device is partially attached to the intravascular device delivery system, but before it is drawn into or towards the valve cover or outer sheath. In one embodiment, guiding member 818 can be a funnel-shaped C-cone.

Deployment of the Valve Device

Figure 22A:
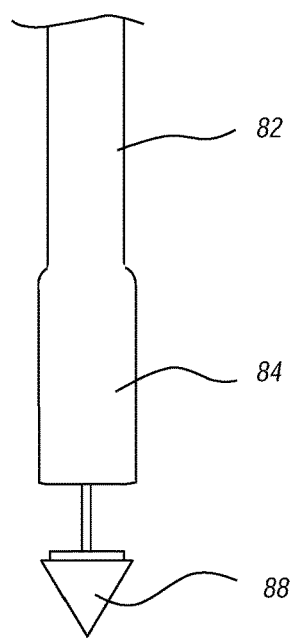
FIGS. 22A through 22F illustrate deployment and release of the replacement heart valve at the mitral annulus.
Figure 22B:
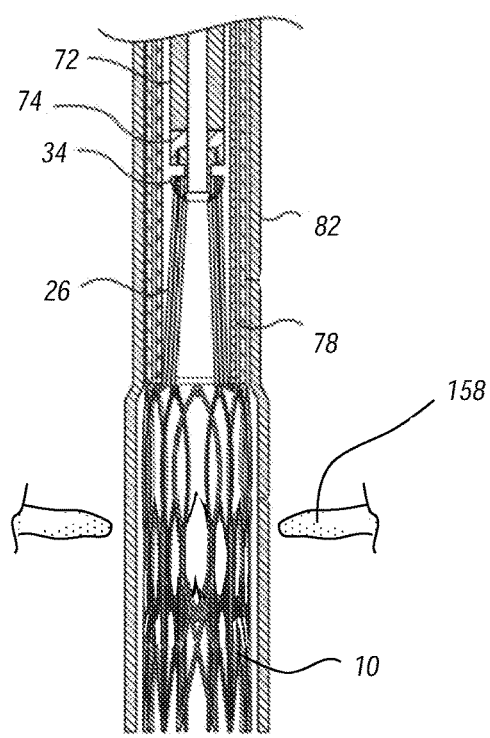
Figure 22C:
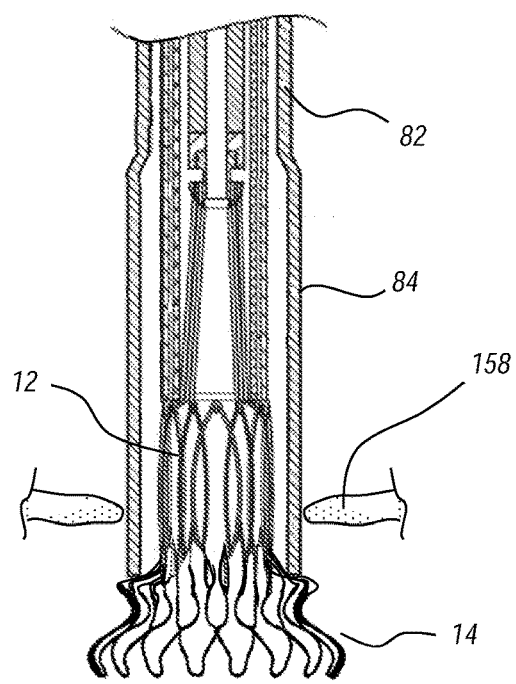
Figure 22D:
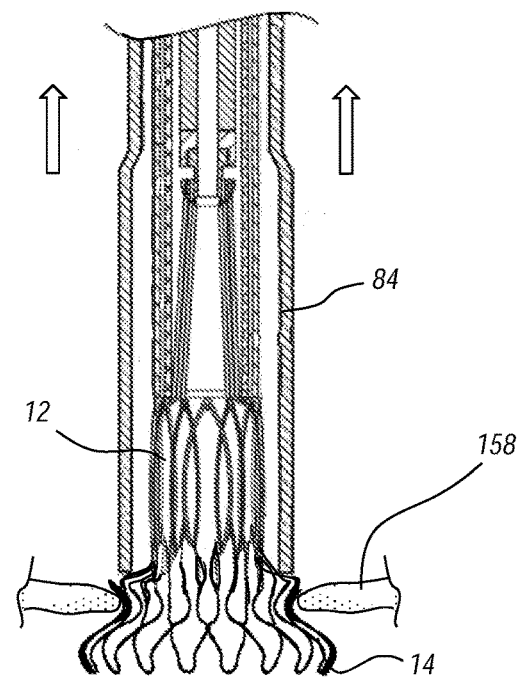

FIGS. 22A through 22F schematically illustrate deployment and release of the valve 10 at the mitral annulus 158. As shown in FIG. 22A, the distal tip 88 is first advanced relative to the outer sheath 82 and valve cover 84 to provide sufficient space for deployment. For clarity, in following Figures, the tip 88 is not shown. FIG. 22B shows in cross-section the delivery member in position at the mitral annulus 158, with a distal portion of the valve 10 positioned on the ventricular side, and a proximal portion of the valve 10 positioned on the atrial side. Partial retraction of the outer sheath 82, as shown in FIG. 22C, allows the ventricular anchor 14 to release and expand. As shown in FIG. 22D, the valve 10 may then be retracted proximally to bring the ventricular anchor 14 into firm contract against the mitral annulus 158. This may be accomplished by retracting the delivery catheter 78. Alternatively, the entire delivery member 70 may be retracted.

Figure 22E:
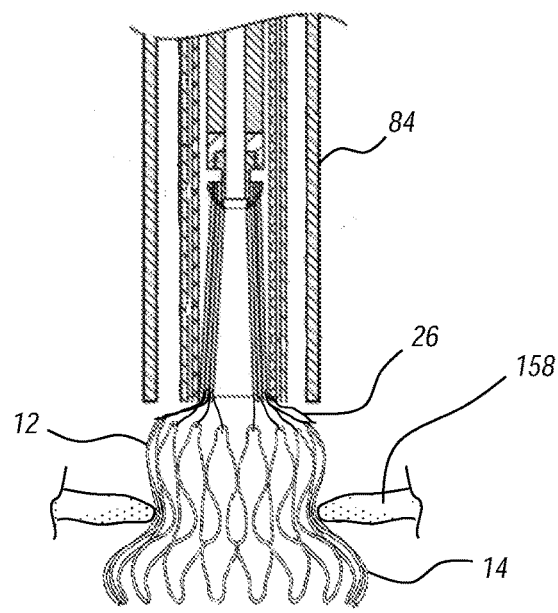
Figure 22F:
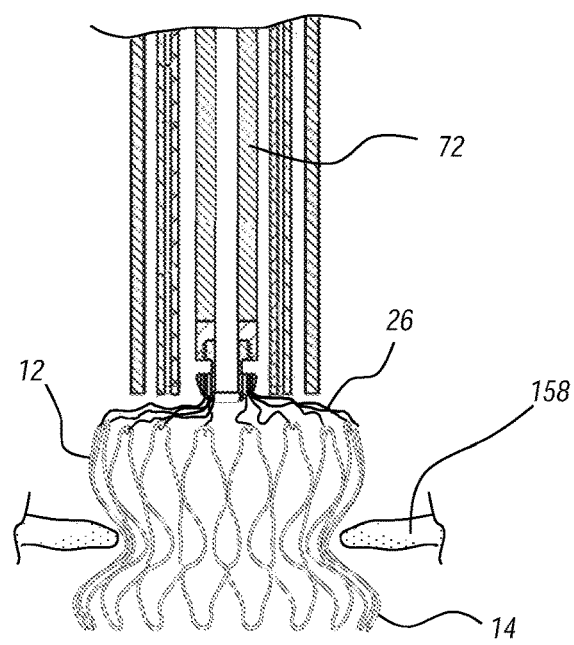

As shown by FIG. 22E, the valve cover 84 may then be further retracted to release the atrial anchor 12 on the atrial side of the mitral annulus 158. At this point, the valve 10 is still held by the suture loops 26 and is not yet fully deployed. This allows the valve 10 to be further positioned or recaptured if necessary. As shown in FIG. 22F, the suture catheter 72 may then be distally advanced to relieve tension in the suture loops 26, allowing the atrial anchor 12 to more fully release and expand. Even further distal advancement of the delivery catheter detaches the suture loops 26 and allows the delivery member 70 to be removed from the patient. The longitudinal position of the tip 88 relative to the suture catheter 72 can be adjusted as needed while the suture catheter 72 is advanced. After the valve 10 is detached, the tip 88 is retracted and reconnected to the valve cover 84 prior to removal of the delivery member from the patient.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that deviate by less than 5%, 1%, 0.1%, or 0.01% of a stated value.

Further, elements described in relation to any embodiment depicted and/or described herein may be substituted for or combined with elements described in relation to any other embodiment depicted and/or described herein. The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

The invention claimed is:

1. A delivery system for intravascularly delivering a replacement heart valve to a targeted cardiac valve, the delivery system comprising:
 an expandable replacement heart valve;
 a handle assembly; and
 an elongated delivery member coupled to the handle assembly and extending distally from the handle assembly, the delivery member having a distal end and being configured to detachably couple to the expandable replacement heart valve at the distal end, the delivery member further including:
- an outer sheath having a valve cover configured to constrain the valve in a compressed configuration;
- a steering component configured to steer the delivery member to enable intravascular delivery of the delivery member to the targeted cardiac valve;
- a delivery catheter configured to longitudinally translate the valve relative to the outer sheath; and
- a suture catheter having one or more tethers configured to detachably couple to a proximal section of the valve, the suture catheter being longitudinally translatable relative to the delivery catheter to enable adjustment of tension in the one or more tethers.

2. The delivery system of claim 1, wherein the steering component is a steering catheter nested within the outer sheath.

3. The delivery system of claim 1, wherein the delivery catheter includes a distal cap configured in size and shape to constrain a proximal section of the replacement valve when the replacement valve is held in the compressed configuration, the distal cap thereby relieving expansion pressure against an inner surface of the valve cover.

4. The delivery system of claim 3, wherein the distal cap has a length to diameter ratio sufficient to maintain coaxial alignment of a distal end of the delivery catheter within the elongated delivery member.

5. The delivery system of claim 4, wherein the length to diameter ratio is greater than or equal to 1.

6. The delivery system of claim 3, wherein an outer circumferential wall of the distal cap tapers in thickness from greater thickness proximally to less thickness distally.

7. The delivery system of claim 1, wherein the suture catheter is nested within the delivery catheter.

8. The delivery system of claim 1, wherein the suture catheter includes a connecting ring detachably connected to a distal end of the suture catheter, a plurality of tethers being coupled to the connecting ring and extending distally from the connecting ring, each tether connecting to a corresponding attachment point of the replacement heart valve.

9. The delivery system of claim 8, wherein the suture catheter includes a hypotube section disposed proximal of the connecting ring, the hypotube section including a plurality of cuts for increasing the flexibility of the hypotube section.

10. The delivery system of claim 8, wherein the connecting ring includes a tapered, angular distal surface.

11. The delivery system of claim 8, wherein the connecting ring has a central lumen longitudinally extending through a center of the connecting ring and a plurality of holes radially spaced about a periphery of its distal end, the plurality of tethers being coupled to the plurality of holes.

12. The delivery system of claim 1, wherein the outer sheath includes a friction-reducing coating on an inner surface of the outer sheath.

13. The delivery system of claim 1, wherein the delivery catheter includes a proximal section and a distal section, and wherein the distal section is formed as a compression coil.

14. The delivery system of claim 13, wherein the delivery catheter is configured to provide a distal force of at least about 50 pounds.

15. A delivery system for intravascularly delivering a replacement mitral valve to the mitral annulus, the delivery system comprising:
- a handle assembly;
- an expandable replacement heart valve; and
- an elongated delivery member coupled to the handle assembly and extending distally from the handle assembly, the delivery member having a distal end and being configured to detachably couple to an expandable replacement heart valve at the distal end, the delivery member further including:
  - an outer sheath having a valve cover configured to constrain the valve in a compressed configuration;
  - a steering catheter nested within the outer sheath;
  - a delivery catheter also nested within the outer sheath, the delivery catheter being configured to longitudinally translate the valve relative to the outer sheath and relative to the steering catheter, the delivery catheter including a proximal section and a distal section, wherein the distal section of the delivery catheter is formed as a stacked coil; and
  - a suture catheter nested within the delivery catheter, the suture catheter including a plurality of tethers extending distally from a distal end of the suture catheter, each tether connecting to a corresponding attachment point of an atrial portion of the replacement valve, the suture catheter being longitudinally translatable relative to the delivery catheter to enable adjustment of tension in the tethers.

16. The delivery system of claim 15, wherein the delivery catheter includes a distal cap configured in size and shape to constrain the atrial portion of the replacement valve when the replacement valve is held in the compressed configuration, the distal cap thereby relieving expansion pressure against an inner surface of the valve cover.

17. The delivery system of claim 15, the suture catheter further comprising a connecting ring detachably connected to the distal end of the suture catheter, the plurality of tethers being coupled to the connecting ring.

18. A method of deploying a replacement heart valve at a targeted mitral valve, the method comprising:
- providing a delivery system, the delivery system including an expandable replacement heart valve, a handle assembly, and an elongated delivery member coupled to the handle assembly and extending distally from the handle assembly, the delivery member having a distal end and being configured to detachably couple to the expandable replacement heart valve at the distal end, the delivery member further including:
  - an outer sheath having a valve cover configured to constrain the valve in a compressed configuration;
  - a delivery catheter configured to longitudinally translate the valve relative to the outer sheath; and
  - a suture catheter having a plurality of tethers configured to detachably couple to a proximal section of the valve, the suture catheter being longitudinally translatable relative to the delivery catheter to enable adjustment of tension in the tethers;
- intravascularly delivering the elongated delivery member to the targeted mitral valve;
- retracting the outer sheath relative to the delivery catheter to allow the replacement heart valve to expand, the replacement heart valve being positioned such that a distal portion is disposed on a ventricular side of the mitral valve, a proximal portion is disposed on an atrial side of the mitral valve, and a central portion is interposed between the distal portion and the proximal portion at the annulus of the mitral valve; and
- translating the suture catheter relative to the delivery catheter to lessen tension in the tethers and allow release of the replacement heart valve from the elongated delivery member.

19. The method of claim 18, wherein each one of the plurality of tethers is attachable to a corresponding attachment point at the proximal portion of the replacement heart valve.

20. The method of claim 18, wherein the step of retracting the outer sheath relative to the delivery catheter further comprises retracting the outer sheath a first amount to expose the ventricular ring of the replacement heart valve, moving the replacement heart valve proximally to bring the ventricular portion into contact with the ventricular side of the mitral valve annulus, and subsequently retracting the outer sheath a second amount to expose the atrial portion of the replacement heart valve.

\* \* \* \* \*